(12) United States Patent
Cui et al.

(10) Patent No.: US 9,233,971 B2
(45) Date of Patent: Jan. 12, 2016

(54) LIPOMACROCYCLES AND USES THEREOF

(76) Inventors: Kunyuan Cui, Bothell, WA (US); Dong Liang, Everett (CN)

( * ) Notice: Subject to any disclaimer, the term of this patent is extended or adjusted under 35 U.S.C. 154(b) by 0 days.

(21) Appl. No.: 13/819,147

(22) PCT Filed: Aug. 26, 2011

(86) PCT No.: PCT/US2011/049463
§ 371 (c)(1),
(2), (4) Date: Feb. 26, 2013

(87) PCT Pub. No.: WO2012/027727
PCT Pub. Date: Mar. 1, 2012

(65) Prior Publication Data
US 2013/0156851 A1    Jun. 20, 2013

Related U.S. Application Data

(60) Provisional application No. 61/377,244, filed on Aug. 26, 2010, provisional application No. 61/384,880, filed on Sep. 21, 2010.

(51) Int. Cl.
| | |
|---|---|
| *C07D 487/22* | (2006.01) |
| *C07D 257/02* | (2006.01) |
| *C07D 255/02* | (2006.01) |
| *C07D 259/00* | (2006.01) |
| *A61K 47/48* | (2006.01) |
| *C12N 15/87* | (2006.01) |
| *C07D 295/13* | (2006.01) |

(52) U.S. Cl.
CPC ............ *C07D 487/22* (2013.01); *A61K 47/481* (2013.01); *A61K 47/48053* (2013.01); *A61K 47/48092* (2013.01); *C07D 255/02* (2013.01); *C07D 257/02* (2013.01); *C07D 259/00* (2013.01); *C07D 295/13* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 5,994,536 | A | 11/1999 | Petrov et al. |
| 2007/0248537 | A1 | 10/2007 | Yang et al. |

FOREIGN PATENT DOCUMENTS

WO    WO-2009/129385 A1    10/2009

*Primary Examiner* — Frederick Krass
*Assistant Examiner* — Celeste A Roney
(74) *Attorney, Agent, or Firm* — Rabin & Berdo, P.C.

(57) ABSTRACT

What is described are macrocyclic compounds formed by reaction of a cyclic compound, which contains an amine, with an epoxide. The macrocyclic compound has the following structure:

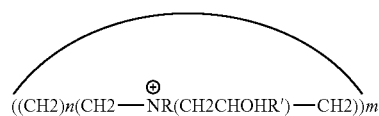

When substituents R and R' that are hydrophobic substituents, the macrocyclic compound functions as a lipid and is compatible with lipid systems, including liposomes and lipid particles. When present in certain lipid systems, the macrocyclic compound enhances the ability of the lipid system to facilitate delivery of therapeutic molecules to target cells in a mammalian subject.

50 Claims, No Drawings

LIPOMACROCYCLES AND USES THEREOF

CROSS REFERENCE TO RELATED APPLICATIONS

This application claims the benefit of the filing dates of U.S. provisional application Ser. No. 61/377,244, filed Aug. 26, 2010, and U.S. provisional application No. 61/384,880, filed Sep. 21, 2010.

TECHNICAL FIELD

Novel lipomacrocycle compounds with multifunctional tails have been synthesized. Lipid-nucleotide particles comprising these compounds have been prepared. The presence of these compounds in the particles enhances knockdown of gene expression.

BACKGROUND

Delivery of therapeutic compounds to a subject is limited by the ability of these compounds to reach and enter targeted organs, tissues, and cells. Delivery of many therapeutic molecules has been found to be facilitated by lipid based delivery vehicles. Lipid-based systems generally involve liposomes or lipid particles. Lipid systems can consist of an aqueous interior surrounded by a lipid bilayer. Lipid particles and lipid bilayers consist of a hydrophobic region and a region that interfaces with water. The hydrophobic region generally consists of alkyl chains of the lipids. The polar region generally consists of charged or polar head groups of the lipids. Lipids form these structures spontaneously because of their amphiphilic character.

Liposomes or lipid particles transport therapeutic molecules in their interior, either in aqueous or hydrophobic regions, and/or on their surface. Liposomes or lipid particles may stabilize a therapeutic molecule both before and after administration to subject organisms. Liposomes may also facilitate delivery to the target tissue or organ, either systemically, e.g., in the circulation, or locally, e.g., when administered topically. Liposomes or lipid particles may also facilitate entry of a therapeutic molecule into the cytoplasm of target cells. The mechanism underlying these phenomena are incompletely understood.

Polynucleotides are an important class of therapeutic molecules. These are generally either DNA or RNA, but include a variety of modified forms, including single- and double-stranded regions. Delivery of polynucleotides, particularly double stranded RNA, is enhanced by lipid systems, either in the form of liposomes or lipid particles. Lipid particles and liposomes are capable of complexing with polynucleotides. The interaction between lipids and polynucleotides can be based on a charge complex. That is, each nucleotide of a polynucleotide carries a negative charge of a phosphate group. If the lipid is positively charged, it may complex with a charge group of a polynucleotide. Similarly, polynucleotides may complex with the polar region of a lipid bilayer. Liposomes and lipid particles may encapsulate polynucleotides or complex with them on their polar or charged surface.

Even though such lipid-polynucleotide particles have shown such great promise, little is known about how lipids and liposomes facilitate delivery of polynucleotides. While certain liposomal compositions have been found to be favorable for transport of polynucleotides to target cells, results are unpredictable, and may vary according to the process of producing the lipid particles or liposomes, and between one preparation and another made by the same process. The efficiency of delivery by a liposomal preparation varies substantially between organs. Efficient delivery in cultures of cells in vitro cannot predict whether the same preparations will enhance delivery when administered to an organism in vivo.

Cationic lipids of the lipid particles and liposomes have been found to be critical for their ability to enhance delivery of therapeutic molecules in general, and polynucleotides in particular. The bases for the critical role of cationic lipids in these systems is incompletely understood and structure function relationships are unknown; their enhancing affect may stem from one or more factors, including the ability of cationic lipids to complex with polynucleotides, their effect on the lipid bilayer structure, their ability to fuse with plasma membranes of the target cell, and/or their ability to facilitate entry of the polynucleotide into the cytoplasm of the cell. This uncertainty creates further unpredictability in this field of research.

The number of naturally occurring cationic lipids is limited. Further, the cost of natural lipids can be substantial, particularly when linked to a large-scale manufacturing process under regulatory conditions. This is because natural lipids are generally extracted and are heterogeneous, and are not synthesized. Homogeneous preparations of single natural lipids are now available commercially, albeit in limited numbers and limited to research use. However, design of novel cationic lipids has shown promise of improving delivery of lipid-based vehicles. There exists a continuing need to identify classes of cationic lipids that enhance lipid-based delivery systems, particularly ones that allow formulations with therapeutic molecules to be readily and reproducibly manufactured.

SUMMARY

What is described is a macrocyclic compound produced by reacting a cyclic compound of formula I

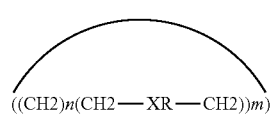

with an epoxide of formula II or III

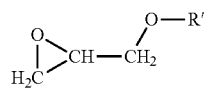

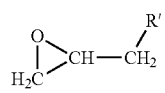

In formula I, X is N, O or S, and may vary within the cyclic compound. When X is O or S, then R is nothing. When X is N, then R is selected from a group consisting of H, a linear or branched alkyl, an aryl, a cholesterol, CH2CONH2, CH2CONHCH3, a methylene bridge between a pair of the amino groups of the cyclic compound, or an ethylene bridge between pairs of amino groups of the cyclic compound. More than one R group may occur in the cyclic compound. The CH2-XR—CH2 group of the cyclic compound repeats from m=2 to 10 times. For every repeat of the CH2-XR—CH2 group, n is 0 or 1. In formula II and III, R is C1 to C20.
In one aspect of the description, the macrocyclic compound comprises at least one amine. Examples of the macrocyclic compound are those with cyclic compound include molecules having the following formulae:
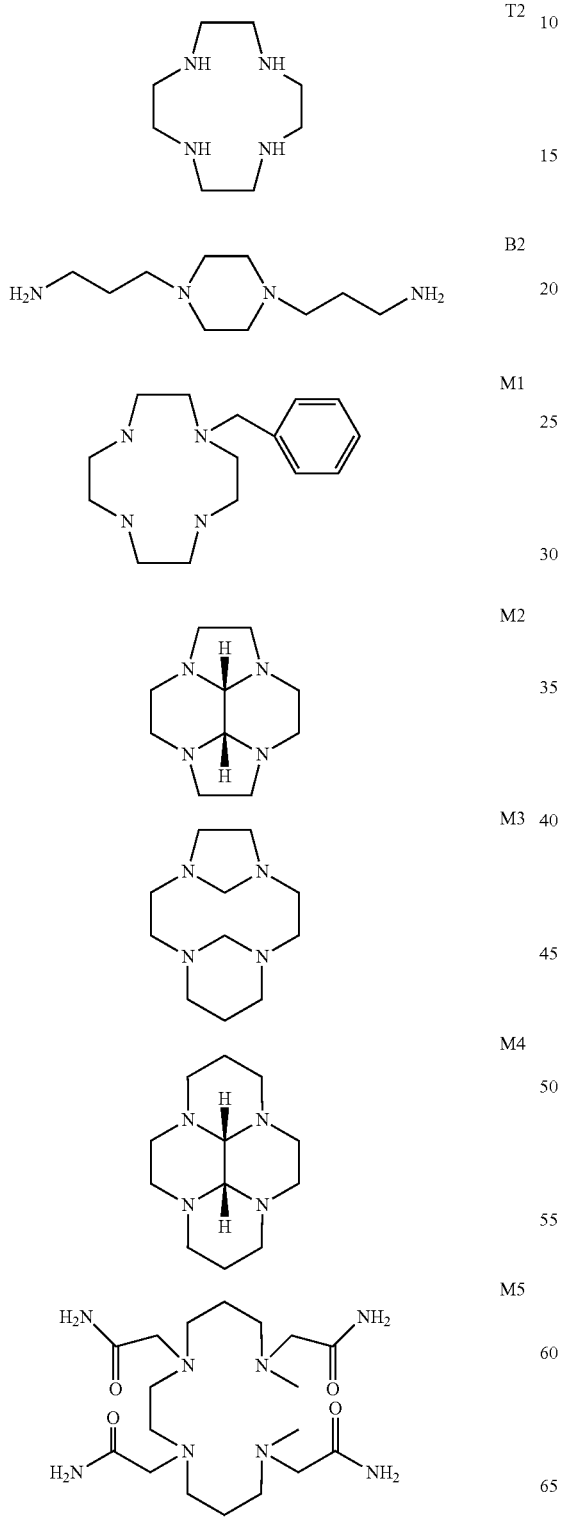
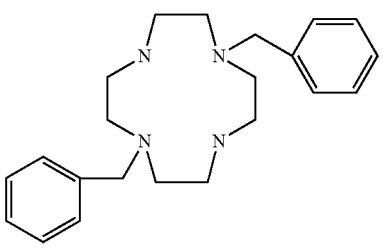
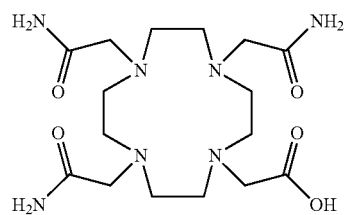
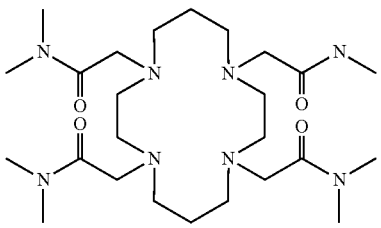
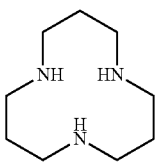
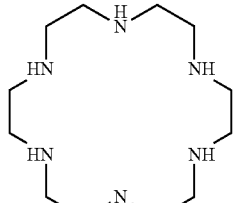
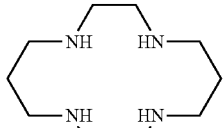
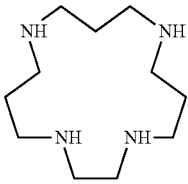

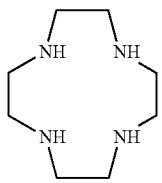

The macrocyclic compound in an aqueous solution at neutral pH has molecular structure of formula IV:

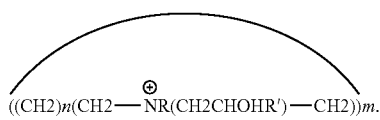

The compound may contain a tertiary or quaternary ammonium group, depending on whether R is H or another substituent. If tertiary, the macrocyclic compound is ionizable.

Another aspect of the description is the macrocyclic compound in which the cyclic compound is reacted with an amount of epoxide that is proportional to the number of amines in the cyclic compound. A macrocyclic compound will accordingly have all amine derivatized. Alternatively, the cyclic compound may be reacted with an amount of epoxide that is less than the number of amines in the cyclic compound, in which some of the amines will not be derivatized. When the cyclic compound is reacted with an amount of epoxide that is proportional to the amount of the cyclic compound (a 1:1 molar ratio), only a single amine will be derivatized.

Preferred macrocyclic compounds are ones with amines derivatized with molecular substituents that include:

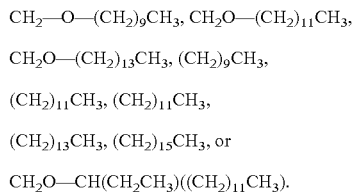

The macrocyclic compound may consist of a heterogeneous set of R substituents or the R substituents may all be the same. Similarly, the X atoms may all be the same or heterogeneous.

Another aspect of the description is the macrocyclic compound in an aqueous solution comprising a polynucleotide. Moreover, the macrocyclic compound may be a component in a lipid-polynucleotide particle comprising a lipid and a polynucleotide. The polynucleotide may be an RNA molecule, for example a siRNA molecule.

Another aspect of the description is the macrocyclic compound in an aqueous solution comprising a liposome or a lipid particle. The macrocyclic compound may be a component of a liposome or a lipid particle. The liposome or lipid particle may be in an aqueous formulation, including one that comprises a polynucleotide. The polynucleotide may be an siRNA molecule. Further, the aqueous formulation is a pharmaceutical composition.

DETAILED DESCRIPTION OF ILLUSTRATIVE EMBODIMENTS

Definitions of technical terms provided herein should be construed to include without recitation those meanings associated with these terms known to those skilled in the art, and are not intended to limit the scope of the disclosure.

An emulsion is a mixture of two immiscible (unblendable) substances. One substance (the dispersed phase) is dispersed in the other (the continuous phase). Emulsions are unstable and thus do not form spontaneously. Energy input through shaking, stirring, homogenizers, or spray processes are needed to form an emulsion.

A self-emulsifying lipid/nucleic acid complex is a complex of lipids and nucleic acid that forms an emulsion in an aqueous environment without the input of substantial energy such as sonication, homogenization etc.

It will be appreciated that the compounds, as described herein, may be substituted with any number of substituents or functional moieties. In general, the term "substituted" whether proceeded by the term "optionally" or not, and substituents contained in formulas of this description, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this description, heteroatoms such as nitrogen may have hydrogen substituents and/or any permissible substituents of organic compounds described herein which satisfy the valences of the heteroatoms. Furthermore, this description is not intended to be limited in any manner by the permissible substituents of organic compounds. Combinations of substituents and variables envisioned by this description are preferably those that result in the formation of stable compounds useful in the treatment of diseases or disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the description contain 1-20 aliphatic carbon atoms. In certain other embodiments, the alkyl, alkenyl, and alkynyl groups employed in the description contain 1-10 aliphatic carbon atoms. In yet other embodiments, the alkyl, alkenyl, and alkynyl groups employed in the description contain 1-8 aliphatic carbon atoms. In still other embodiments, the alkyl, alkenyl, and alkynyl groups employed in the description contain 1-6 aliphatic carbon atoms. In yet other embodiments, the alkyl, alkenyl, and alkynyl groups employed in the description contain 1-4 carbon atoms. The term "alkyl" as used herein refers to saturated, straight- or branched-chain hydrocarbon radicals derived from a hydrocarbon moiety containing between one and twenty carbon atoms by removal of a single hydrogen atom. The term "alkenyl" denotes a monovalent group derived from a hydrocarbon moiety having at least one carbon-carbon double bond by the removal of a single hydrogen atom. The term "alkynyl" as used herein refers to a monovalent group derived form a hydrocarbon having at least one carbon-carbon triple bond by the removal of a single hydrogen atom.

The term "alkoxy," or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the description contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the description contains 1-8 aliphatic carbon atoms. In still other embodiments, the aliphatic group contains 1-6 aliphatic carbon atoms. In yet other embodiments, the aliphatic group contains 1-4 aliphatic carbon atoms. The term "carboxylic acid" as used herein refers to a group of formula —CO2H.

Cyclic compounds including macrocyclic compounds as used herein, refers to a non-aromatic partially unsaturated or fully saturated 3 or more-membered ring system which include 3 or more atoms in size and bi and tri-cyclic ring system which may include aromatic six-membered aryl or aromatic heterocyclic groups fused or linked to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

As used herein, the term interfering nucleic acid (iNA) refers to a nucleic acid duplexes having a sense and antisense strand, which when entered into a RISC complex induces enzymatic degradation of mRNA. Generally each strand contains predominantly RNA nucleotides but the strands can contain RNA analogs, RNA and RNA analogs, RNA and DNA, RNA analogs and DNA, or one strand that is completely DNA and one strand that is RNA as long as the iNA construct induces enzymatic degradation of a homologous mRNA.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. By "RNA" is meant a molecule comprising at least one ribonucleotide residue. By "ribonucleotide" is meant a nucleotide with a hydroxyl group at the 2' position of a .βD-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the iNA or internally, for example at one or more nucleotides of the RNA. Nucleotides in the RNA molecules of the instant description can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of a iNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other). There are several examples of modified nucleic acid bases known in the art. By "modified bases" in this aspect is meant nucleotide bases other than adenine, guanine, cytosine and uracil at 1' position or their equivalents.

As used herein the term small interfering RNA (siRNA), sometimes known as short interfering RNA or silencing RNA, is used to refer to a class of double-stranded RNA molecules, 16-29 nucleotides in length, that play a variety of roles in biology. Most notably, siRNA is involved in the RNA interference (RNAi) pathway, where it interferes with the expression of a specific gene. In addition to their role in the RNAi pathway, siRNA also act in RNAi-related pathways, e.g., as an antiviral mechanism or in shaping the chromatin structure of a genome; the complexity of these pathways is only now being elucidated.

The term phospholipids refer to any of various compounds composed of fatty acids and phosphoric acid and a nitrogenous base, Examples of phospholipids include but are not limited to phosphatidyl ethanolamine, phosphatidyl choline, phosphatidyl inositol and diphosphatidyl glycerol, such as 1,2-Dilauroyl-sn-glycerol (DLG); 1,2-Dimyristoyl-sn-glycerol (DMG); 1,2-Dipalmitoyl-sn-glycerol (DPG); 1,2-Distearoyl-sn-glycerol (DSG); 1,2-Dilauroyl-sn-glycero-3-phosphatidic acid (sodium salt; DLPA); 1,2-Dimyristoyl-sn-glycero-3-phosphatidic acid (sodium salt; DMPA); 1,2-Dipalmitoyl-sn-glycero-3-phosphatidic acid (sodium salt; DPPA); 1,2-Distearoyl-sn-glycero-3-phosphatidic acid (sodium salt; DSPA); 1,2-Diarachidoyl-sn-glycero-3-phosphocholine (DAPC); 1,2-Dilauroyl-sn-glycero-3-phosphocholine (DLPC); 1,2-Dimyristoyl-sn-glycero-3-phosphocholine (DMPC); 1,2-Dipalmitoyl-sn-glycero-O-ethyl-3-phosphocholine (chloride or triflate; DPePC); 1,2-Dipalmitoyl-sn-glycero-3-phosphocholine (DPPC); 1,2-Distearoyl-sn-glycero-3-phosphocholine (DSPC); 1,2-Dilauroyl-sn-glycero-3-phosphoethanolamine (DLPE); 1,2-Dimyristoyl-sn-glycero-3-phosphoethanolamine (DMPE); 1,2-Dipalmitoyl-sn-glycero-3-phosphoethanolamine (DPPE); 1,2-Distearoyl-sn-glycero-3-phosphoethanolamine (DSPE); 1,2-Dilauroyl-sn-glycero-3-phosphoglycerol (sodium salt; DLPG); 1,2-Dimyristoyl-sn-glycero-3-phosphoglycerol (sodium salt; DMPG); 1,2-Dimyristoyl-sn-glycero-3-phospho-sn-1-glycerol (ammonium salt; DMP-sn-1-G); 1,2-Dipalmitoyl-sn-glycero-3-phosphoglycerol (sodium salt; DPPG); 1,2-Distearoyl-sn-glycero-3-phosphoglycero (sodium salt; DSPG); 1,2-Distearoyl-sn-glycero-3-phospho-sn-1-glycerol (sodium salt; DSP-sn-1-G); 1,2-Dipalmitoyl-sn-glycero-3-phospho-L-serine (sodium salt; DPPS); 1-Palmitoyl-2-linoleoyl-sn-glycero-3-phosphocholine (PLinoPC); 1-Palmitoyl-2-oleoyl-sn-glycero-3-phosphocholine (POPC); 1-Palmitoyl-2-oleoyl-sn-glycero-3-phosphoglycerol (sodium salt; POPG); 1-Palmitoyl-2-oleoyl-sn-glycero-3-phosphoglycerol (sodium salt; POPG); 1-Palmitoyl-2-oleoyl-sn-glycero-3-phosphoglycerol (ammonium salt; POPG); 1-Palmitoyl-2-4-o-sn-glycero-3-phosphocholine (P-lyso-PC); 1-Stearoyl-2-lyso-sn-glycero-3-phosphocholine (S-lyso-PC); 1,2-didocosahexaenoyl-sn-glycero-3-phosphoethanolamine (22:6 PE); 1,2-diarachidonoyl-sn-glycero-3-phosphoethanolamine (20:4 PE); 1,2-dilinolenoyl-sn-glycero-3-phosphoethanolamine (18:3 PE); 1,2-dilinoleoyl-sn-glycero-3-phosphoethanolamine (DlinPE) 1,2-dipalmitoyl-sn-glycero-3-phosphoethanolamine (DPPE); 1,2-distearoyl-sn-glycero-3-phosphoethanolamine (DSPE); 1,2-dimyristoyl-sn-glycero-3-phosphoethanolamine (DMPE); and mixtures thereof.

Lipomacrocycles and Uses Thereof

The description relates in part to synthesis of lipomacrocycle compounds with multifunctional tails. The compounds are particularly suitable for delivering polynucleotides to cells and tissues as demonstrated in subsequent sections. The lipomacrocycle compound described herein may be used for other purposes as well as, for example, recipients and additives.

Lipomacrocycle compounds with multifunctional tails can be synthesized as described herein by reacting amine with one or more functional molecules, forming tails of the lipomacrocycle compounds.

The synthetic methods for the lipomacrocycle compound can be synthesized with the skills in the art. The skilled of the arts will recognize other methods to produce these compounds, and to produce also the other compounds of the description.

The lipomacrocycle compounds may be prepared by a) an amine reacting with cholesteryl chioroformate, epoxy terminal aliphatic compounds and polymers, separately to form amine-cholesterol, amine-aliphatic and amine-polymer lipomacrocycle respectively; b) the products from above step can further used to produce lipomacrocycle containing two functional groups and c) the product from C can be further used to synthesize lipomacrocycle containing all of three different functional tails (steroids, aliphatic chain and polymer. Each functional group can be mono, di, tri, and more substituted depending on the reaction sites of amine compound chosen for the synthesis.

A polymer can be added to the compound containing both sterol(s) and aliphatic chain(s) to produce a multifunctional tailed compounds containing cholesterol moiety (ies), aliphatic chain (s) and a polymer for a simplified drug encapsulation and effective drug delivery. An amine and a tail compound may be reacted at low temperature first in the presence of solvent to prepare the lipomacrocycle compounds modified from the method mentioned above. Alternatively, an amine and a tail compound may be reacted at elevated temperatures in the absence of solvent to prepare the lipomacrocycle compounds modified from the method mentioned above. Typically, the amines chosen contain between two and more amine moieties, and sterol compound, most commonly is cholesterol and the epoxide-terminated compounds include a tail of varying chain lengths and optionally feature various functional groups and varying degrees of saturation PEG-epoxide.

The macrocyclic compound chosen may contain between two and more amine moieties, e.g., a cholesterol. The epoxide compounds may include a tail of varying chain lengths and optionally feature various functional groups and varying degrees of saturation or a polymer with varying lengths and optionally feature various functional or targeting groups. Two different aliphatic compounds or polymers may be used in the reaction mixture to prepare a lipomacrocycle compound with multifunctional tails.

Examples of cyclic compounds to be used to produce lipomacrocyclic compounds are:

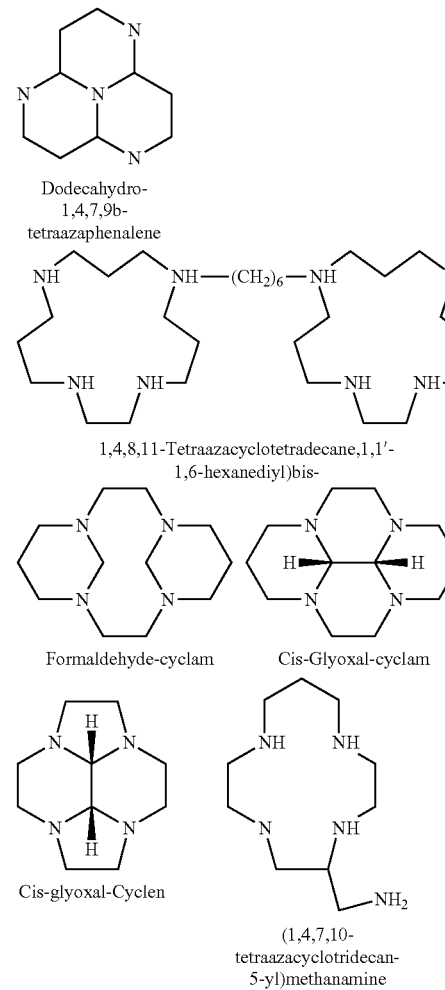

-continued
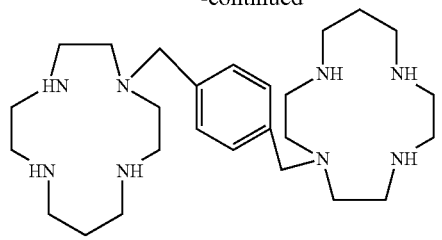
1,4-bis(1,4,7,10-tetraazacyclotridecan-4-yl)methyl)
benzene
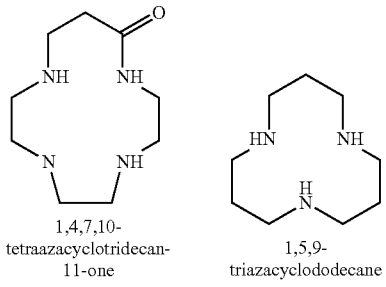
1,4,7,10-
tetraazacyclotridecan-
11-one
1,5,9-
triazacyclododecane
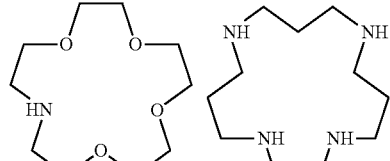
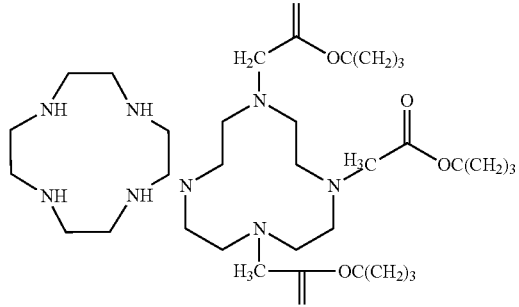
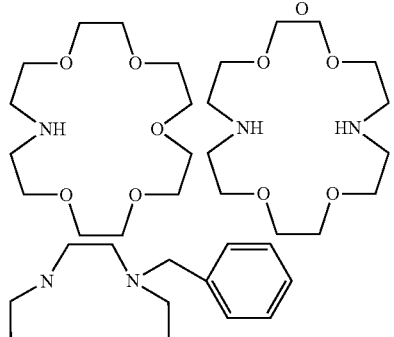
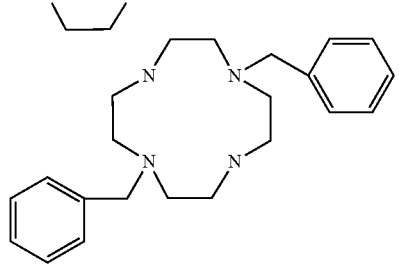
-continued
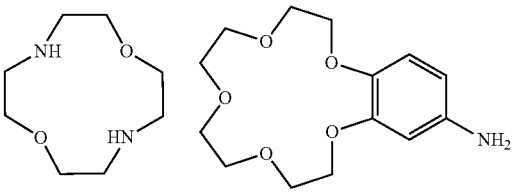
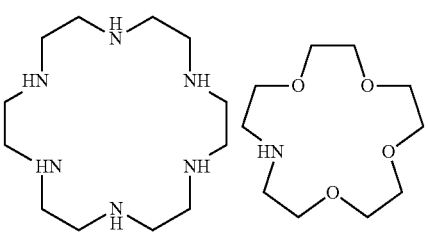
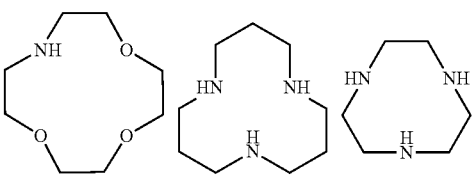
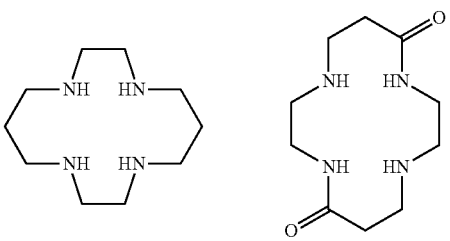
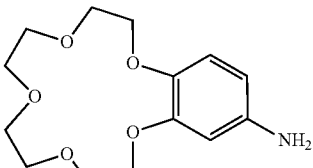
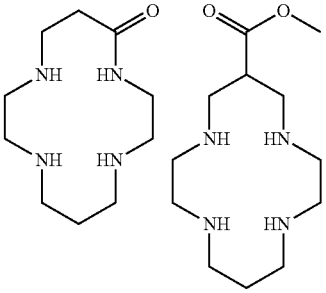
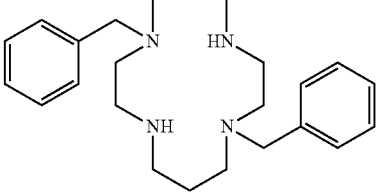

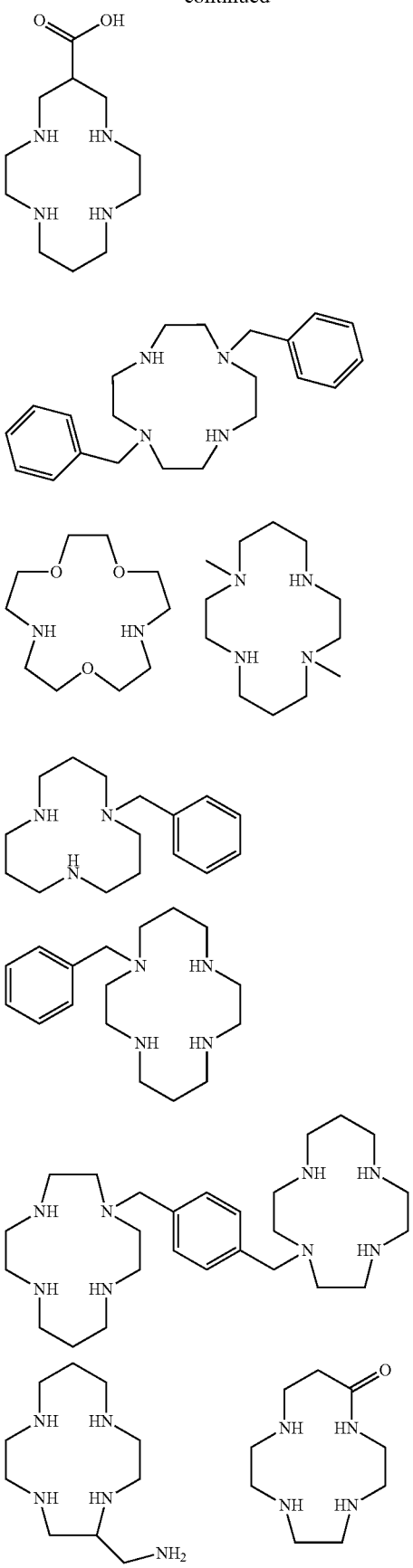

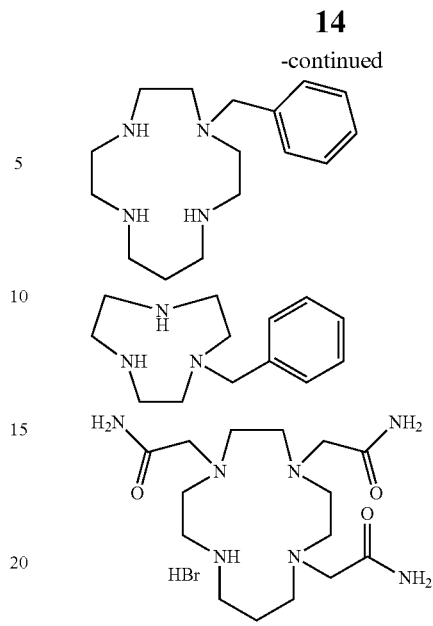

The lipomacrocycle compounds may be combined with an agent to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The lipomacrocycle compounds may be combined with other lipomacrocycle compounds, polymers (synthetic or natural), surfactants, cholesterol, carbohydrates, proteins, lipids, etc. to form the particles. These particles may then optionally be combined with a pharmaceutical excipient to form a pharmaceutical composition.

The description also provides libraries of lipomacrocycle compounds prepared by the described methods. These lipomacrocycle compounds may be prepared and/or screened using high-throughput techniques involving liquid handlers, robots, microtiter plates, and computers. In certain embodiments, the lipomacrocycle compounds are screened for their ability to transfect polynucleotides or other agents (e.g., proteins, peptides, small molecules) into the cell.

The present description provides novel lipomacrocycle compounds and drug delivery systems based on the use of such lipomacrocycle compounds. The system may be used in the pharmaceutical/drug delivery arts to delivery polynucleotides, proteins, small molecules, peptides, antigen, drugs, etc. to a patient, tissue, organ, or cell. These novel compounds may also be used as materials for coating, additives, excipients, materials, or bioengineering.

The lipomacrocycle compounds of the present description provide for several different uses in the drug delivery art. The amine-containing portion of the lipomacrocycle compounds may be used to complex polynucleotides, thereby enhancing the delivery of polynucleotide and preventing their degradation. The lipomacrocycle compounds may also be used in the formation of picoparticles, nanoparticles, microparticles, liposomes, and micelles containing the agent to be delivered. Preferably, the lipomacrocycle compounds are biocompatible and biodegradable, and the formed particles are also biodegradable and biocompatible and may be used to provide controlled, sustained release of the agent to be delivered. These and their corresponding particles may also be responsive to pH changes given that these are protonated at lower pH. They may also act as proton sponges in the delivery of an agent to a cell to cause endosome lysis.

The lipomacrocycle compounds of the present description contain primary, secondary, tertiary, and/or quaternary amines, and salts thereof. The amines may be cyclic or acyclic amines. In certain embodiments, the lipomacrocycle compounds are relatively non-cytotoxic. The lipomacrocycle compounds may be biocompatible and biodegradable. The lipomacrocycle may have $pK_a$s in the range of approximately 5.5 to approximately 7.5, more preferably between approximately 6.0 and approximately 7.0. It may be designed to have a desired pKa between approximately 3.0 and approximately 9.0, or between approximately 5.0 and approximately 8.0. The lipomacrocycle compounds described herein are particularly attractive for drug delivery for several reasons: they contain amino groups for interacting with DNA, RNA, other polynucleotides, and other negatively charged agents, for buffering the pH, for causing endo-osmolysis, for protecting the agent to be delivered, they can be synthesized from commercially available starting materials; and/or they are pH responsive and can be engineered with a desired $pK_a$.

A composition containing a lipomacrocycle compound may be 30-70% lipomacrocycle compound, 0-60% cholesterol, 0-30% phospholipid and 1-10% polyethylene glycol (PEG). Preferably, the composition is 30-40% lipomacrocycle compound, 40-50% cholesterol, and 10-20% PEG. In other preferred embodiments, the composition is 50-75% lipomacrocycle compound, 20-40% cholesterol, and 5 to 10% phospholipid, and 1-10% PEG. The composition may contain 60-70% lipomacrocycle compound, 25-35% cholesterol, and 5-10% PEG. The composition may contain up to 90% lipomacrocycle compound and 2 to 15% helper lipid.

The formulation may be a lipid particle formulation, for example containing 8-30% lipomacrocycle compound, 5-30% helper lipid, and 0-20% cholesterol; 4-25% lipomacrocycle, 4-25% helper lipid, 2 to 25% cholesterol, 10 to 35% cholesterol-PEG, and 5% cholesterol-amine; or 2-30% lipomacrocycle, 2-30% helper lipid, 1 to 15% cholesterol, 2 to 35% cholesterol-PEG, and 1-20% cholesterol-amine; or up to 90% lipomacrocycle and 2-10% helper lipids, or even 100% lipomacrocycle.

In certain embodiments, one equivalent of an amine is reacted with one equivalent of an epoxide-terminated compound. In certain embodiments, one equivalent of an amine is reacted with one, two, three, four, five, six or more equivalents of an epoxide-terminated compound. In certain embodiments, the amount of epoxide-terminated compound is limiting to prevent the functionalization of all amino groups. The resulting lipomacrocycle or lipomacrocycle composition in these instances contains secondary amino groups and/or primary amino groups. Lipomacrocycle compounds having secondary amines are particular useful in certain instances. In certain embodiments, amine-containing lipomacrocycle compounds that have not been fully functionalized are further reacted with another electrophile (e.g., terminal epoxide, alkyl halide, etc.). Such further functionalization of the amines of the lipomacrocycle compound results in lipomacrocycle compounds with different epoxide-compound derived tails. One, two, three, four, five, or more tails may be different from the other tails of the lipomacrocycle compounds.

The preferred macrocyclic compound is produced by reacting a cyclic compound consisting of formula I

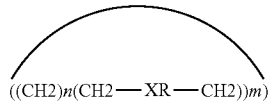

with an epoxide consisting of formula II or III

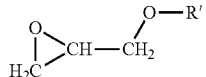

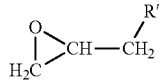

R may be a hydrogen, a substituted, unsubstituted, branched or unbranched $C_2$-$C_{20}$ aliphatic, or a substituted, unsubstituted, branched or unbranched $C_{1-20}$-heteroaliphatic or —$CH_2$ CH(OH)Rh; a steroid, a PUFA, guanidine or arginine, in any combination; and wherein the steroid is selected from the group consisting of lanosterol, ergosterol, desmosterol, a plant phytosterol, such as stigmasterol, or a bile salt or bile salt derivative such as cholic acid, deoxycholic acid, hydrodeoxycholic acid or dehydrocholic acid. $R_1$ is polyethylene glycol (PEG) where molecular weight from 50 to 20,000.

R and R' may be hydrogen. an unsubstituted and unbranched $C_2$-$C_{20}$ aliphatic, an alkyl, e.g., a methyl ethyl, propyl, or butyl, an unsubstituted and unbranched heteroaliphatic, a hetero alkyl, another macrocycle molecule linked to through any linkers, e.g, a hydrocrabon chain, a steroid, e.g., lanosterol, ergosterol, desmosterol, a plant phytosterol, such as stigmasterol, a bile salt or bile salt, e.g., cholic acid, deoxycholic acid, hydrodeoxycholic acid or dehydrocholic acid, or a PEG, e.g., with a molecular weight from 50 to 20,000.

The lipomacrocycle compound of the present description may be derived from a cyclic compound of the formula:

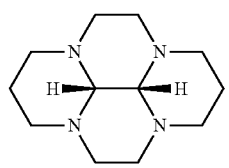

Examples of such lipomacrocycle compounds may include:

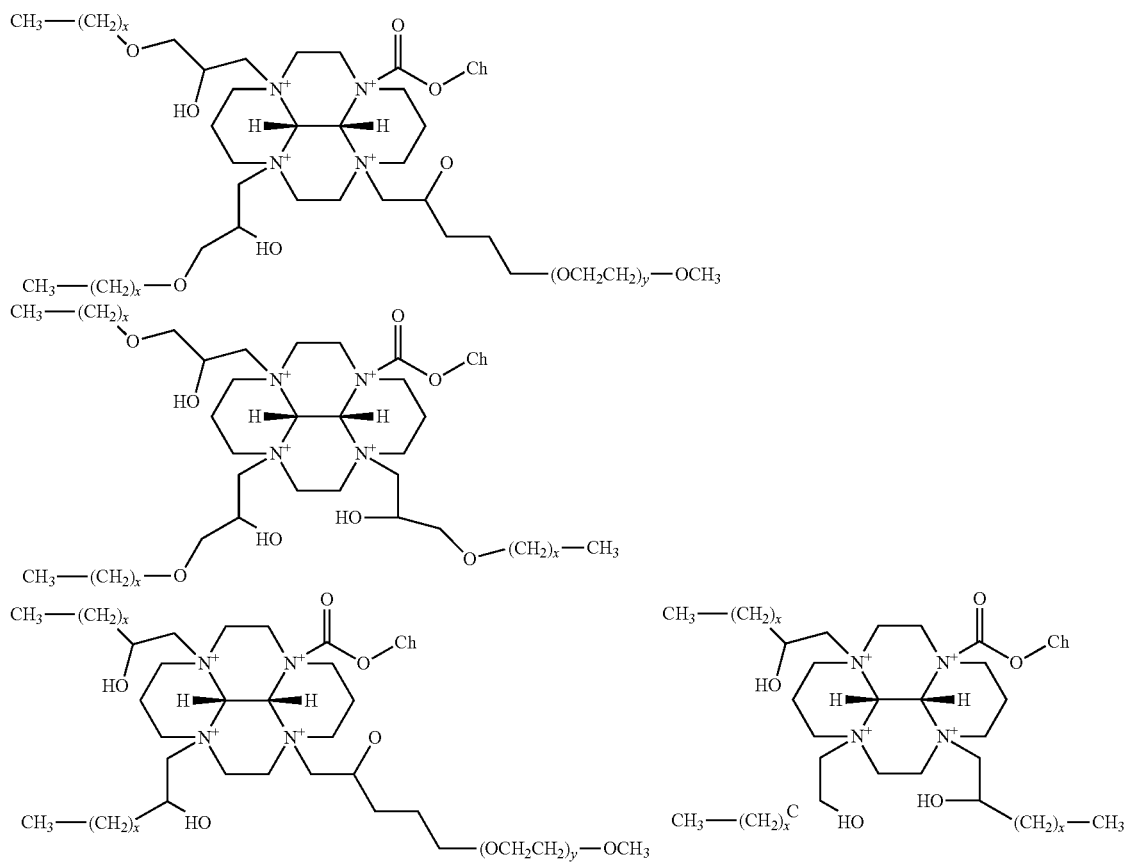
A lipomacrocycle compound of the present description may be of the formula:
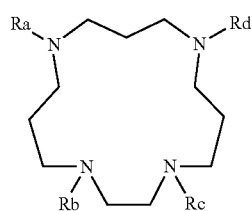
(40)
Specific examples may include:
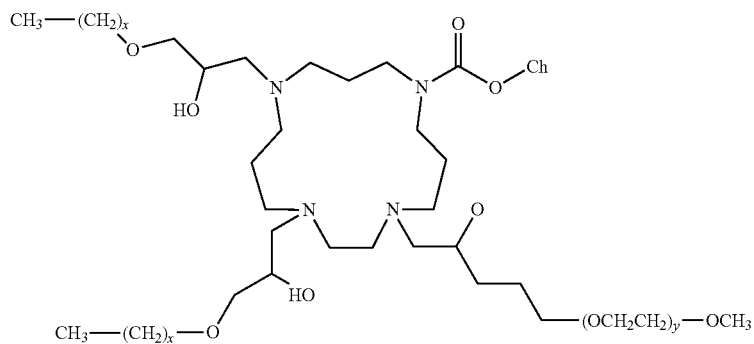

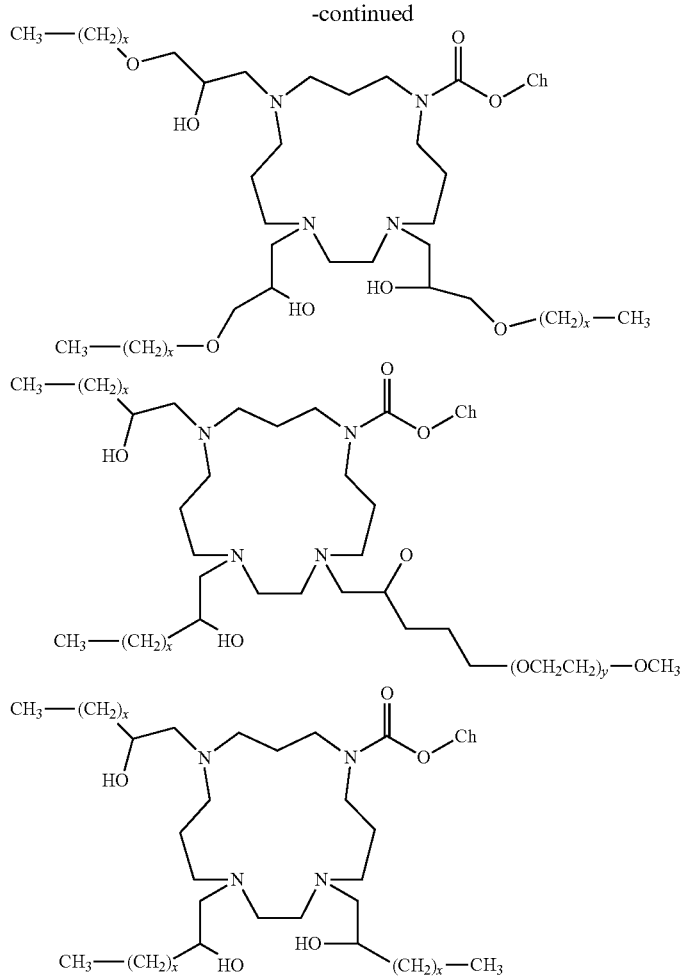
The lipomacrocycle compound of the present description may be of the formula:
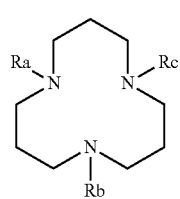
Specific examples may include:
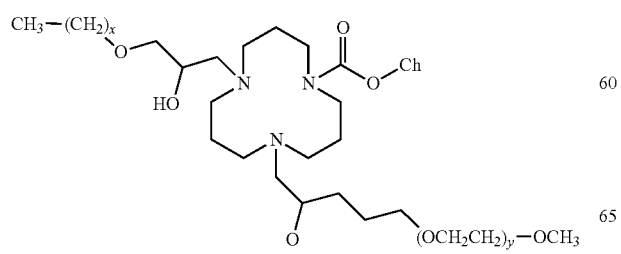
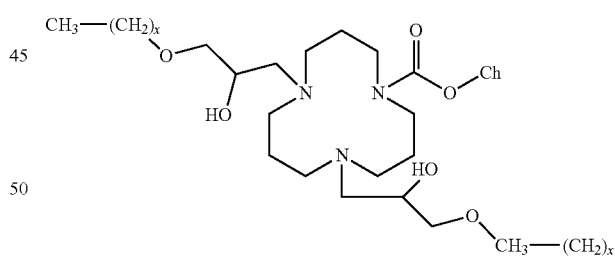
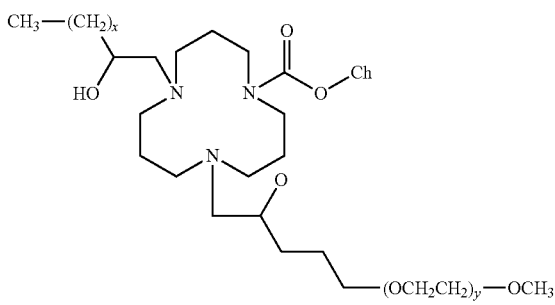

21
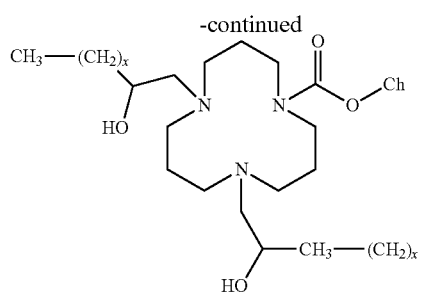
The lipomacrocycle compound of the present description may be of the formula:
22
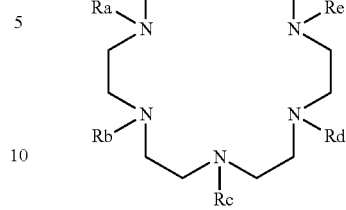
Examples of these compounds may include:
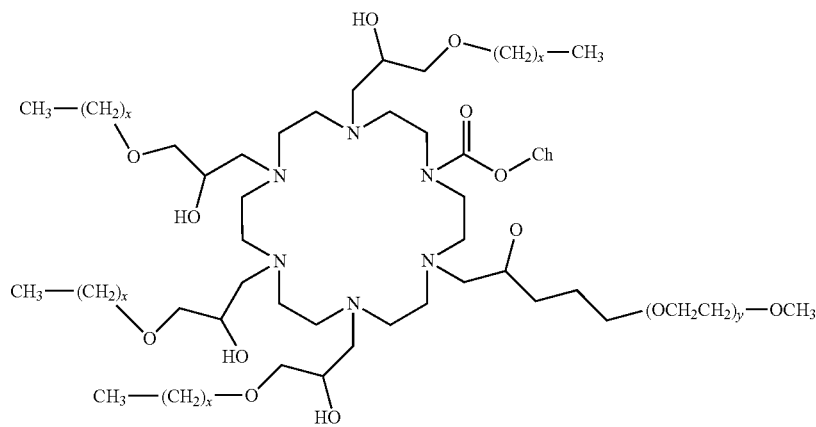
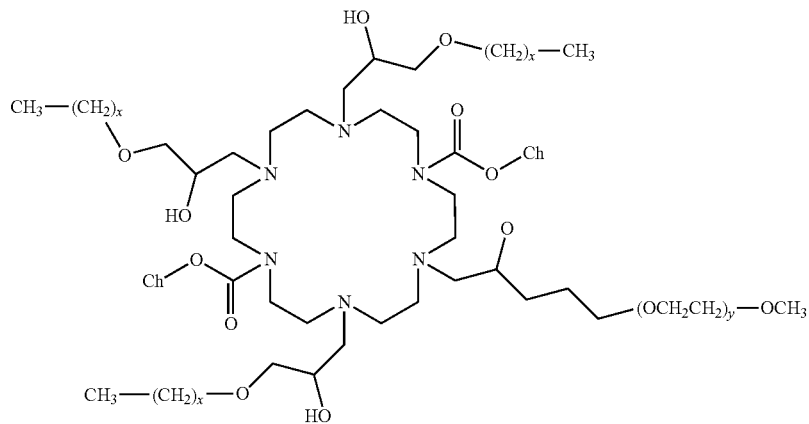
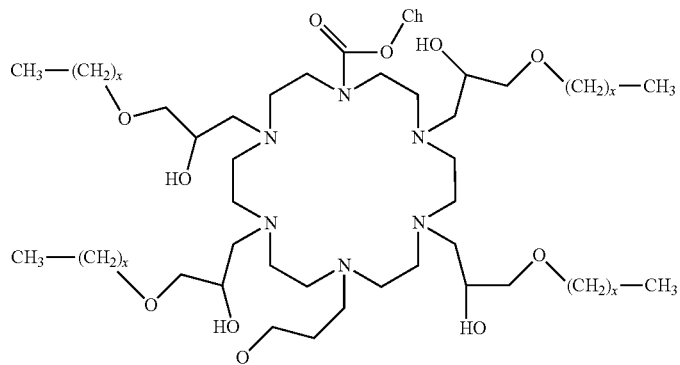

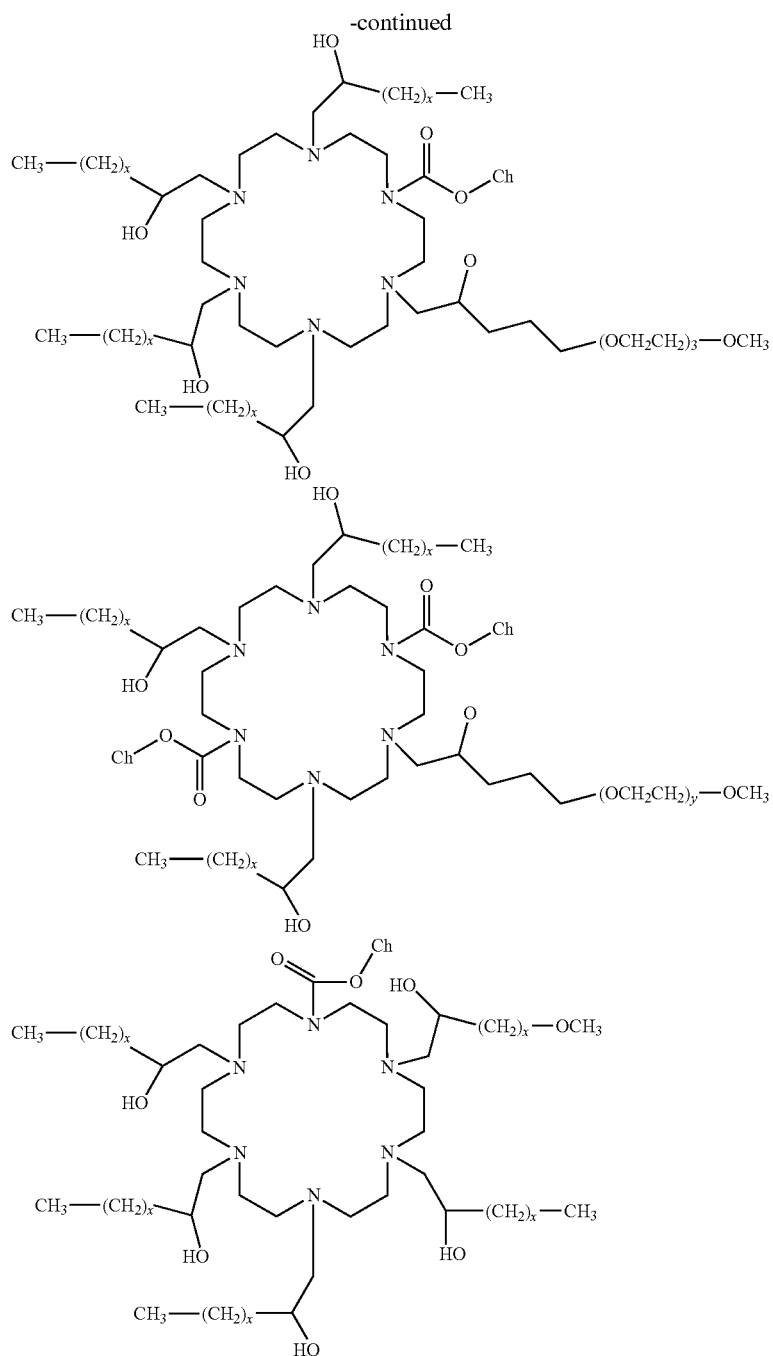
The lipomacrocycle compound of the present description may be of the formula:
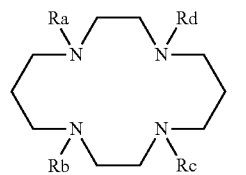

Examples of these compounds may include:
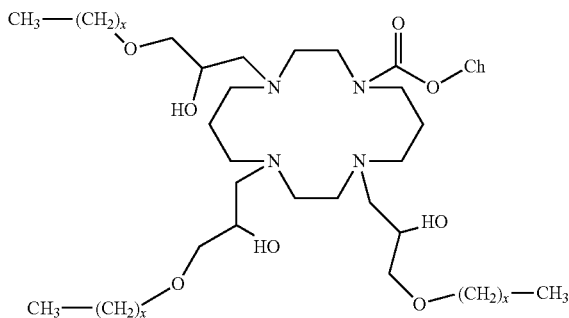
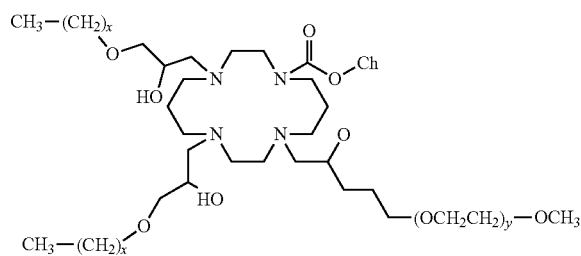
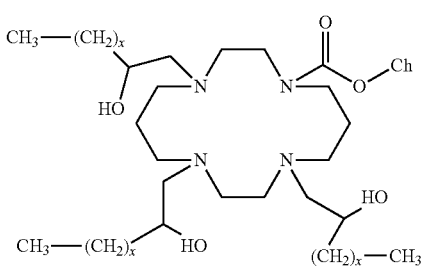
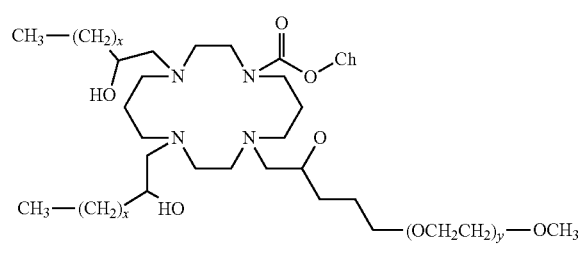
T the lipomacrocycle compound of the present description may be of the formula:
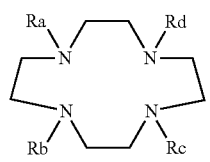
Examples of these compounds may include:
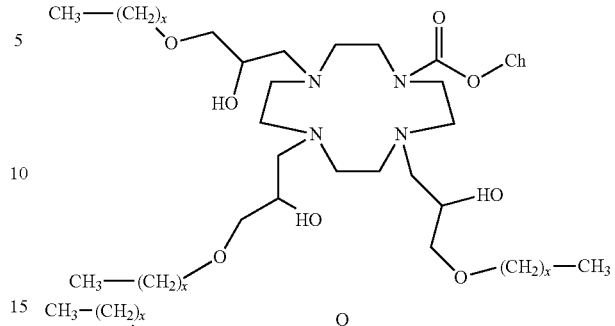
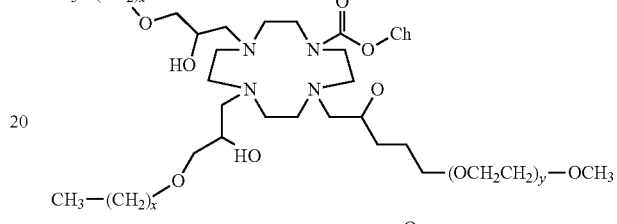
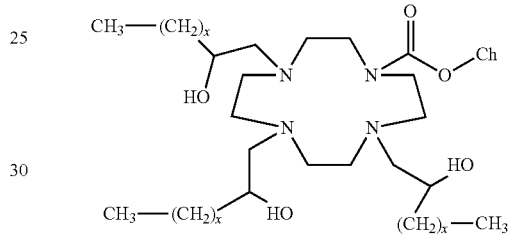
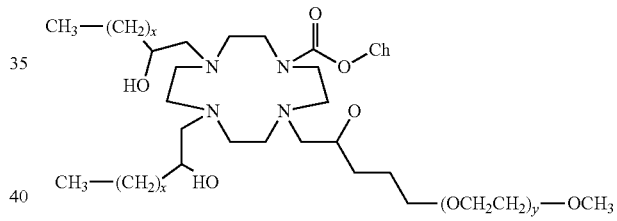
The lipomacrocycle compound may be derived from a cyclic compound of the formulae:
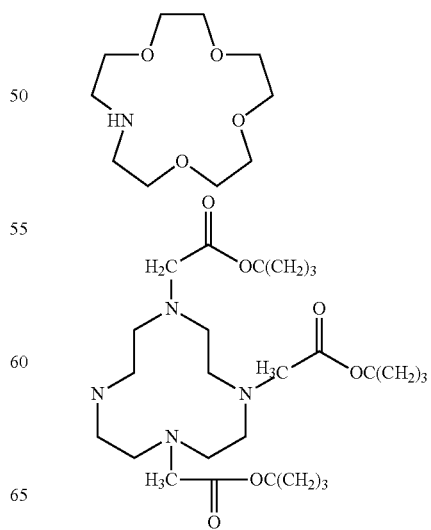

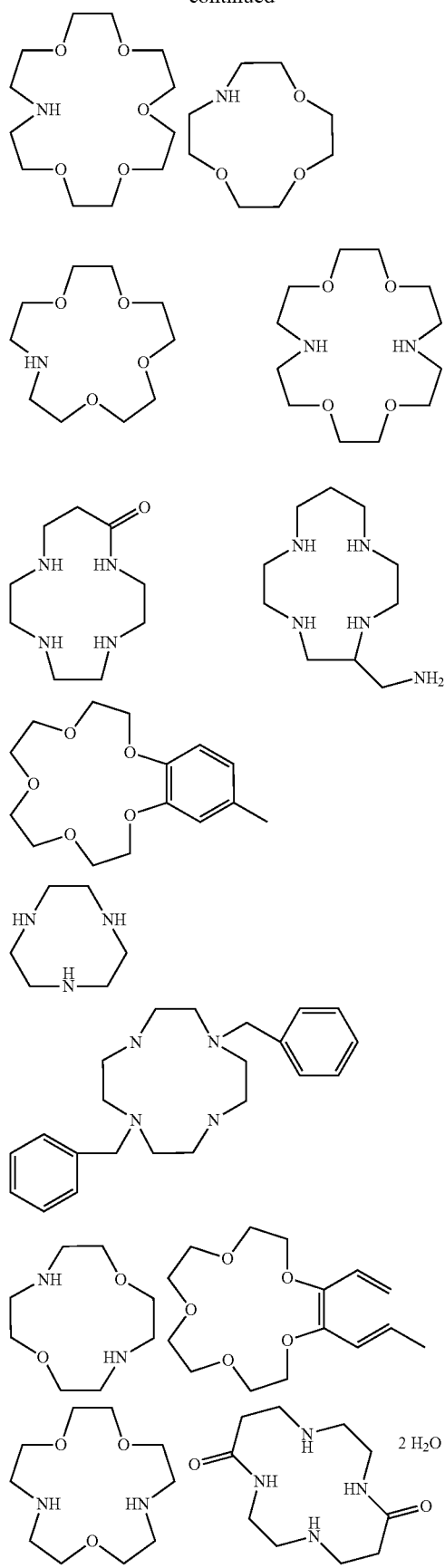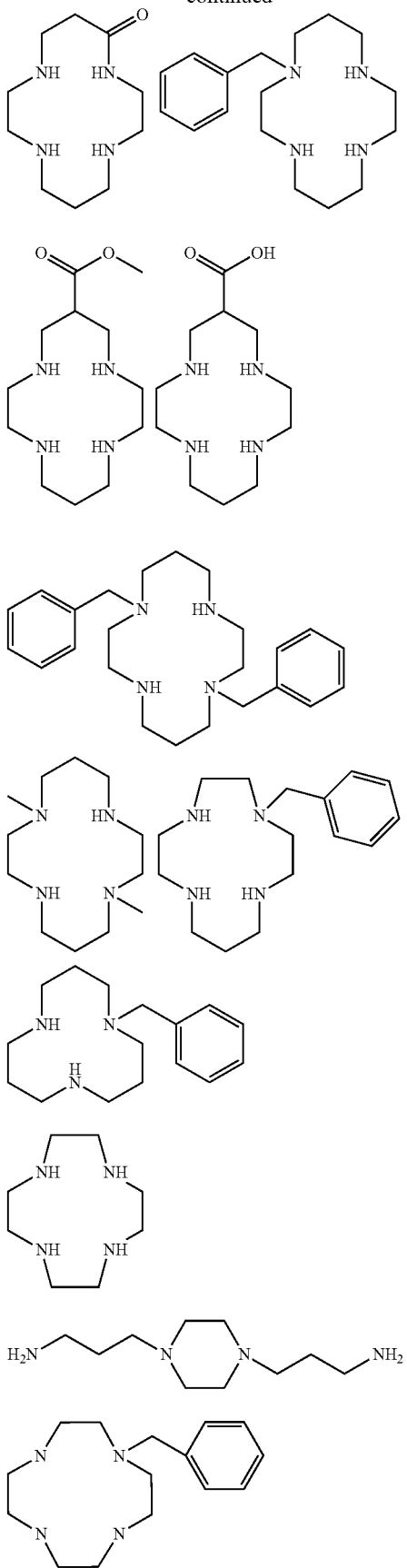

M2
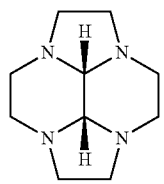
M3
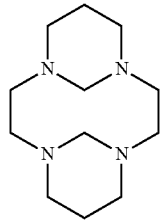
M4
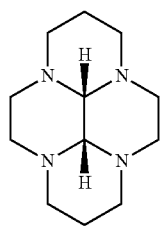
M5
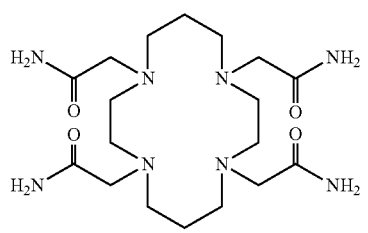
M6
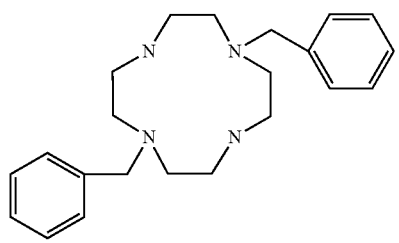
M7
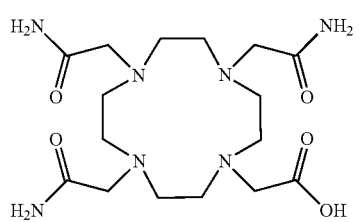
M8
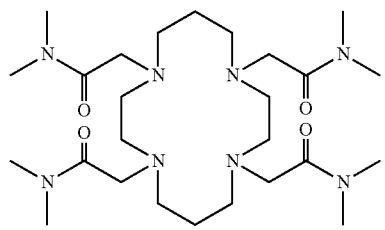
M9
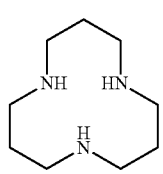
M10
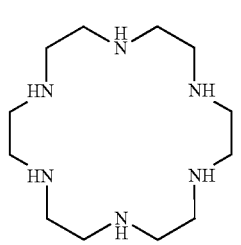
M11
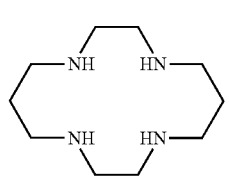
T1
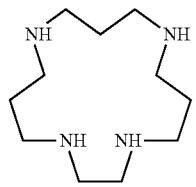
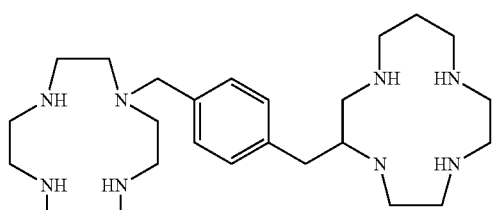
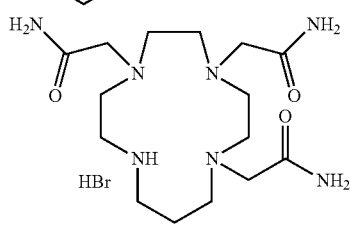
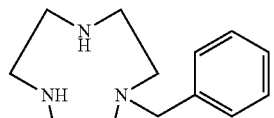
S1
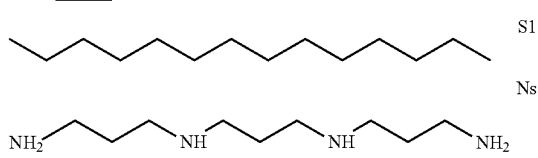
Ns -continued

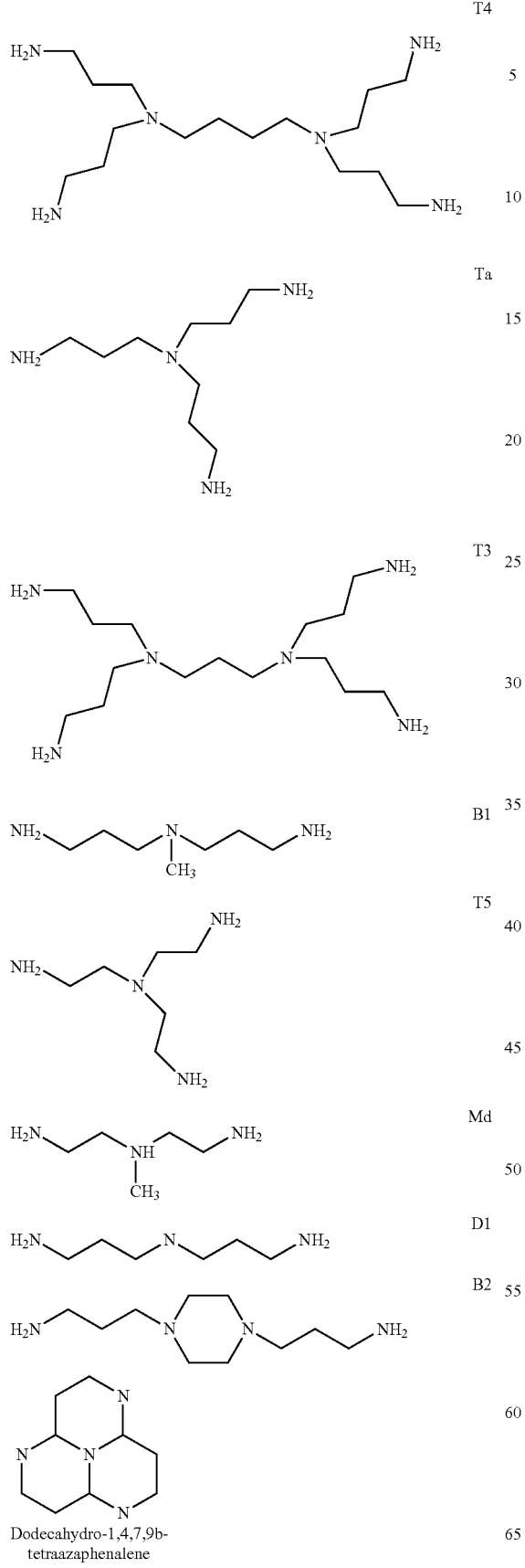

T4

Ta

T3

B1

T5

Md

D1

B2

-continued

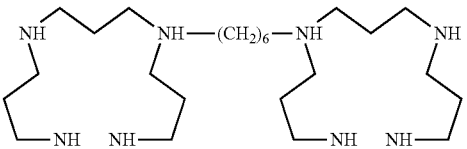

1,4,8,11-Tetraazacyclotetradecane,1,1′-(1,6-hexanediyl)bis-

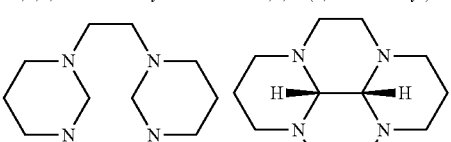

Formaldehyde-cyclam          Cis-Glyoxal-cyclam

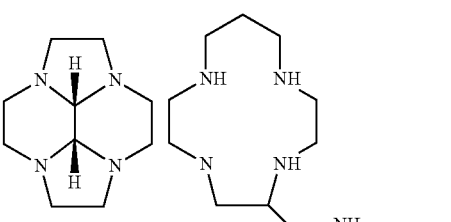

Cis-glyoxal-Cyclen (1,4,7,10-
tetraazacyclotridecan-
5-yl)methanamine

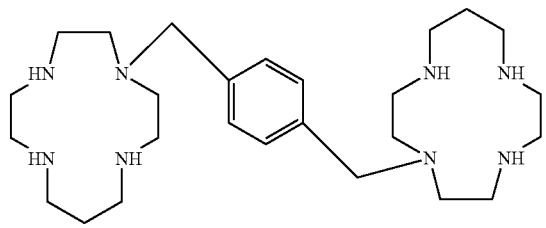

1,4-bis((1,4,7,10-tetraazacyclotridecane-4-yl)methyl)benzene

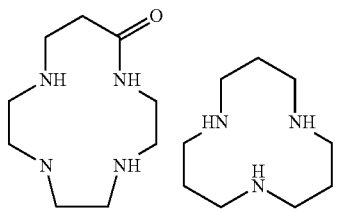 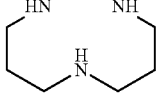

1,4,7,10-
tetraazacyclotridecan-
11-one 1,5,9-
triazacyclododecane

The lipomacrocycle compound may be derived from an epoxide of the following formulae:

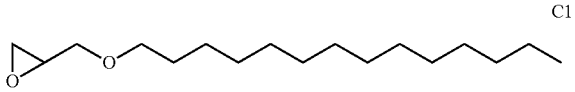

C1

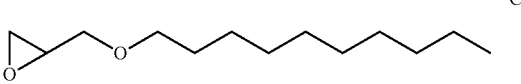

C2

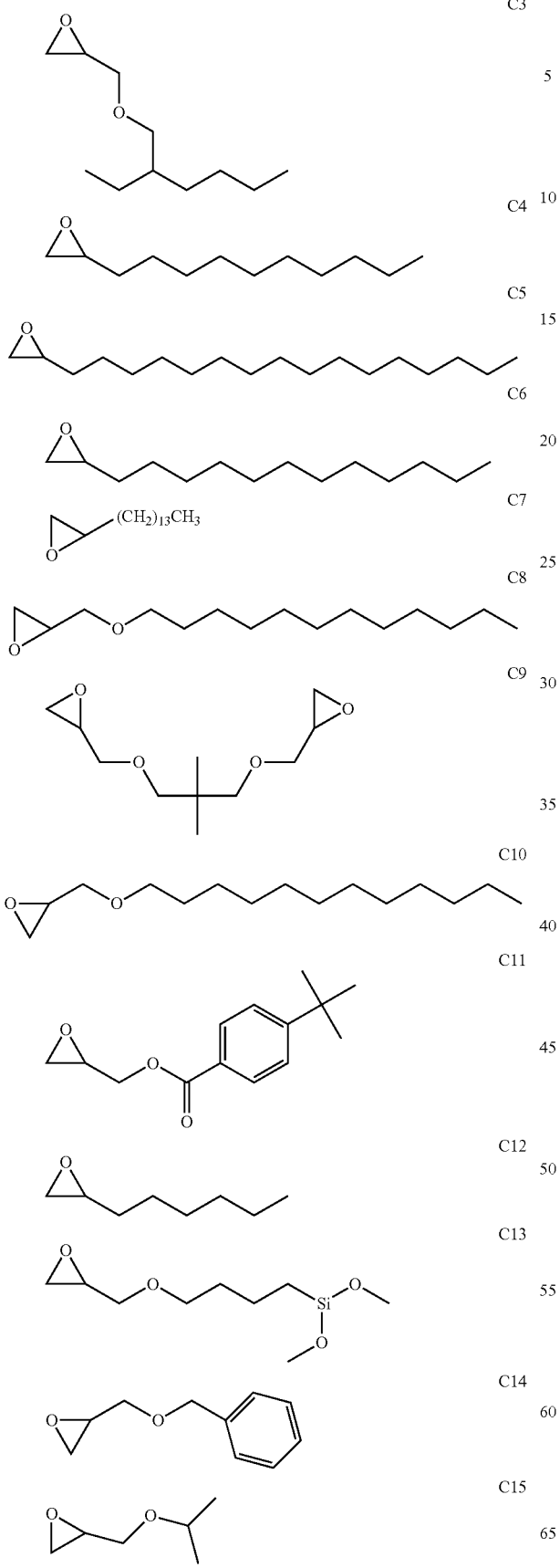
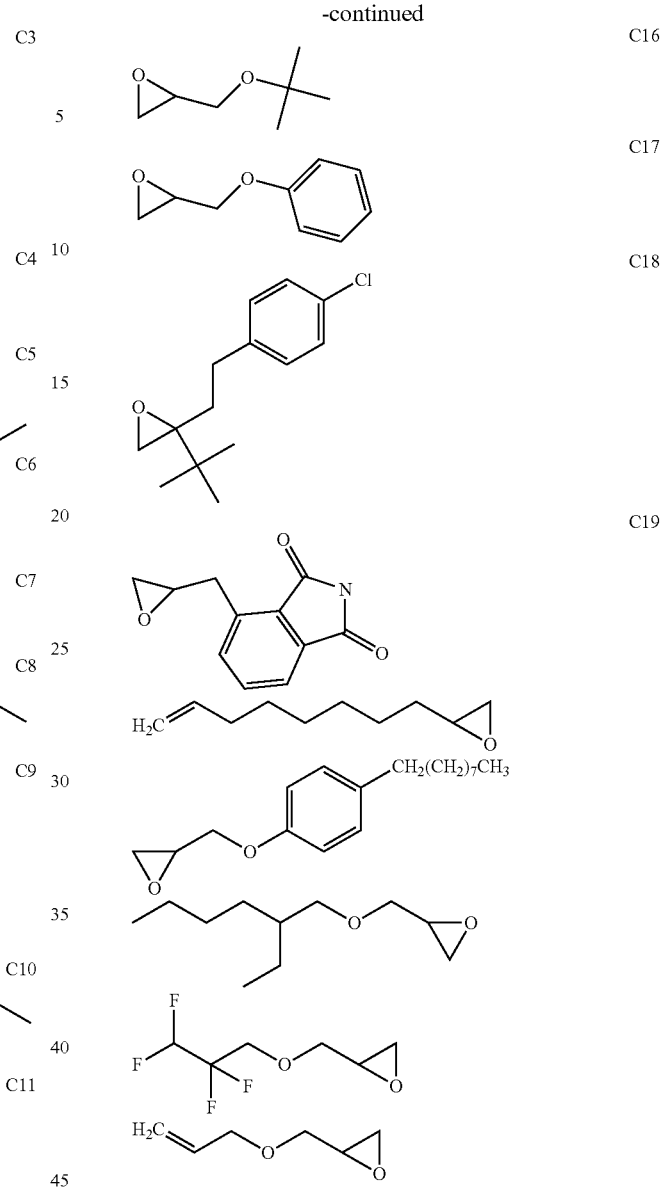

Compositions and Formulations for Administration

The nucleic acid-lipid compositions comprising the lipomacrocycle compounds of this disclosure may be administered by various routes, for example, to effect systemic delivery via intravenous, parenteral, intraperitoneal or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

In some embodiments, this disclosure provides a method of treating a disease or disorder in a mammalian subject. A therapeutically effective amount of a composition of this disclosure containing a nucleic acid, a lipomacrocycle compound, a phospholipid, may be administered to a subject having a disease or disorder associated with expression or overexpression of a gene that can be reduced, decreased, downregulated, or silenced by the composition.

A therapeutically effective amount of a composition of this disclosure containing a nucleic acid, a lipomacrocycle compound and/or a phospholipid and/or cholesterol and/and or a PEG-linked cholesterol may be administered to a subject having a disease or disorder associated with expression or overexpression of a gene that can be reduced, decreased, downregulated, or silenced by the composition.

The nucleic acid may be DNA, RNA, antisense, aptamer, antagamer, plasmid, interfering nucleic acid (iNA), ribozyme, small interfering nucleic acid (siRNA), microRNA (miRNA), or a mixture of these.

The compositions may comprise a phospholipid, e.g., phosphatidylethanolamine, phosphatidylcholine, sphinogomyelin and phosphatidylinositol. The phospholipid may consist of a 12-24 alkyl chain with or without unsatured band(s).

The composition may comprise a PEG-linked lipid, in which the PEG has a molecular weight of 100-10,000 Da, preferably 400-5000 Da, most preferably 2000 Da.

For example, the composition may include the lipomacrocycle compound of the present description and a nucleic acid with: distearoylphosphatidylcholine (DSPC), cholesterol, and dimyristoylglycerol-PEG (DMG-PEG2000); DSPC, cholesterol, and dipalmitoylglycerol-PEG (DPG-PEG2000); DSPC, cholesterol, and distearoylglycerol-PEG (DSG-PEG2000); 1,2-dilinoleoyl-sn-glycero-3-phosphoethanolamine, cholesterol, and DMG-PEG2000; 1,2-dilinoleoyl-sn-glycero-3-phosphoethanolamine (DlinPE), cholesterol, and DPG-PEG2000; DlinPE, cholesterol, and DSG-PEG2000; DSPC, cholesterol, and C16 PEG750 ceramide; DSPC, cholesterol, and cholesterol-PEG; DSPC, cholesterol, and DSPE-PEG 2000; DSPC, cholesterol, and DOPE-PEG 2000; or DSPC, cholesterol, cholesterol-PEG 660, and DSPE-PEG 2000.

Another aspect of the description is lipid mixture in ethanol directly contact with siRNA in water wherein the liposome is spontaneously formed without further processing, wherein the ethanol contents can be kept in very low concentration related to water which can be administered directly into a mammal without removing ethanol.

Another aspect of the description is any of the above compositions suitable for delivery of nucleic acid to skin, or for injection. Any of the above formulations may be suitable for delivery of a therapeutic molecule to the liver, to the lung, to a tumor, or other tissues or organs.

Contacting the nucleic acid solution with the solution of lipids is accomplished by mixing together a solution of nucleic acids, which is typically an aqueous solution, with a solution of the lipids, which is in ethanol, preferentially in equal or smaller volume in comparison with that of nucleic acid, such as 1:1 to 10:1 ratio (water/ethanol). The ethanol can be removed by either evaporation at room temperature or heated the mixture to 50° C. One of the skills of the art is that the ethanol may not be needed to be removed before dosing to animal, if higher ratio of water to ethanol and therefore very small amount of ethanol is in the formulation. Consequently, the very small amount of ethanol in the formulation does not cause any adverse effect and is acceptable for administration. Therefore, with higher water/ethanol ratio, the removal of trace amount of ethanol in the formulation may not be necessary before administration in mammal. One of the skills in the art will understand that this mixing can take place by any number of methods, for example by mechanical means such as by using vortex mixers or injection pumps and stirred reactors.

This disclosure provides pharmaceutically acceptable nucleic acid compositions useful for therapeutic delivery of nucleic acids, DNA, RNA, plasmids, siRNA, miRNA, antisense nucleic acids, ribozymes, aptamers, antagomirs and gene-silencer. These compositions and methods may be used for prevention and/or treatment of diseases in a mammal. The novel method dramatically simplified the nucleic acid formulation process and composition of the description has greatly improved nucleic acid delivery efficiency to the cells.

This disclosure provides pharmaceutically acceptable small molecule compositions useful for therapeutic delivery of small molecule (<1000 Da) such as taxol. These compositions and methods may be used for prevention and/or treatment of diseases in a mammal. The novel method dramatically simplified the small molecule formulation process and composition of the description has greatly improved small molecule delivery efficiency to the cells.

Examples of hydrophobic lipids include molecules such as sterols, such as cholesterol, dioleoylphosphatidylethanolamine, phytosterols such as campesterol, sitosterol, stigmasterol and other hydrophobic lipids known in the art.

Examples of polyethylene glycol (PEG)-linked glycerol lipids includes a PEG-linked 1,2-Dilauroyl-sn-glycerol (DLG); 1,2-Dimyristoyl-sn-glycerol (DMG); 1,2-Dipalmitoyl-sn-glycerol (DPG); 1,2-Distearoyl-sn-glycerol (DSG).

Examples of polyethylene glycol (PEG)-linked cholesterol and PEG-linked derivatives of cholesterol and PEG-linked phytosterols such as PEG-campesterol, PEG-sitosterol and PEG-stigmasterol.

Examples of polyethylene glycol (PEG)-linked phospholipids include a PEG-linked DSPE-PEG, DOPE-PEG, ceramide-PEG, PEG-phsphoethanolamine, and PEG-phosphotidylcholine.

The neutral or zwitteronic lipids can be uses in formulation include but not limited to phosphatidyl ethanolamine, phosphatidyl choline, phosphatidyl inositol and diphosphatidyl glycerol, such as 1,2-Dilauroyl-sn-glycerol (DLG); 1,2-Dimyristoyl-sn-glycerol (DMG); 1,2-Dipalmitoyl-sn-glycerol (DPG); 1,2-Distearoyl-sn-glycerol (DSG); 1,2-Dilauroyl-sn-glycero-3-phosphatidic acid (sodium salt; DLPA); 1,2-Dimyristoyl-sn-glycero-3-phosphatidic acid (sodium salt; DMPA); 1,2-Dipalmitoyl-sn-glycero-3-phosphatidic acid (sodium salt; DPPA); 1,2-Distearoyl-sn-glycero-3-phosphatidic acid (sodium salt; DSPA); 1,2-Diarachidoyl-sn-glycero-3-phosphocholine (DAPC); 1,2-Dilauroyl-sn-glycero-3-phosphocholine (DLPC); 1,2-Dimyristoyl-sn-glycero-3-phosphocholine (DMPC); 1,2-Dipalmitoyl-sn-glycero-O-ethyl-3-phosphocholine (chloride or triflate; DPePC); 1,2-Dipalmitoyl-sn-glycero-3-phosphocholine (DPPC); 1,2-Distearoyl-sn-glycero-3-phosphocholine (DSPC); 1,2-Dilauroyl-sn-glycero-3-phosphoethanolamine (DLPE); 1,2-Dimyristoyl-sn-glycero-3-phosphoethanolamine (DMPE); 1,2-Dipalmitoyl-sn-glycero-3-phosphoethanolamine (DPPE); 1,2-Distearoyl-sn-glycero-3-phosphoethanolamine (DSPE); 1,2-Dilauroyl-sn-glycero-3-phosphoglycerol (sodium salt; DLPG); 1,2-Dimyristoyl-sn-glycero-3-phosphoglycerol (sodium salt; DMPG); 1,2-Dimyristoyl-sn-glycero-3-phospho-sn-1-glycerol (ammonium salt; DMP-sn-1-G); 1,2-Dipalmitoyl-sn-glycero-3-phosphoglycerol (sodium salt; DPPG); 1,2-Distearoyl-sn-glycero-3-phosphoglycero (sodium salt; DSPG); 1,2-Distearoyl-sn-glycero-3-phospho-sn-1-glycerol (sodium salt; DSP-sn-1-G); 1,2-Dipalmitoyl-sn-glycero-3-phospho-L-serine (sodium salt; DPPS); 1-Palmitoyl-2-linoleoyl-sn-glycero-3-phosphocholine (PLinoPC); 1-Palmitoyl-2-oleoyl-sn-glycero-3-phosphocholine (POPC); 1-Palmitoyl-2-oleoyl-sn-glycero-3-phosphoglycerol (sodium salt; POPG); 1-Palmitoyl-2-oleoyl-sn-glycero- 3-phosphoglycerol (sodium salt; POPG); 1-Palmitoyl-2-oleoyl-sn-glycero-3-phosphoglycerol (ammonium salt; POPG); 1-Palmitoyl-2-4-o-sn-glycero-3-phosphocholine (P-lyso-PC); 1-Stearoyl-2-lyso-sn-glycero-3-phosphocholine (S-lyso-PC); 1,2-didocosahexaenoyl-sn-glycero-3-phosphoethanolamine (22:6 PE); 1,2-diarachidonoyl-sn-glycero-3-phosphoethanolamine (20:4 PE); 1,2-dilinolenoyl-sn-glycero-3-phosphoethanolamine (18:3 PE); 1,2-dilinoleoyl-sn-glycero-3-phosphoethanolamine (DlinPE) 1,2-dipalmitoyl-sn-glycero-3-phosphoethanolamine (DPPE); 1,2-distearoyl-sn-glycero-3-phosphoethanolamine (DSPE); 1,2-dimyristoyl-sn-glycero-3-phosphoethanolamine (DMPE); and mixtures thereof.

Another embodiment is the formulation consisting of a variety of ratios of above compositions, preferably, 1 part polynucleotide/3.85 parts lipomacrocycle (any one of lipomacrocycle listed in table 1, 2 and 3 or known in arts)/0.42 parts DSPC/0.21 parts DMG-PEG 2000/0.79 parts cholesterol (weight/weight). Another embodiment is the formulation consisting of 1 part polynucleotide/3.85 parts lipomacrocycle (any one of lipomacrocycles listed in table 1 and 2 or known in arts)/0.42 parts DSPC/0.21 parts DSG-PEG 2000/0.79 parts cholesterol (weight/weight). Another embodiment is the formulation consisting of 1 part polynucleotide/3.85 parts lipomacrocycle (any one of lipoaimne listed in table 1, 2 and 3 or known in arts)/0.42 parts DSPC/0.21 parts DPG-PEG 2000/0.79 parts cholesterol (weight/weight). Another embodiment is the formulation consisting of 1 part polynucleotide/3.85 parts lipomacrocycle (any one of lipomacrocycle listed in table 1, 2 and 3 or known in arts)/0.42 parts DLinPE/0.21 parts DMG-PEG 2000/0.79 parts cholesterol (weight/weight). Another embodiment is the formulation consisting of 1 part polynucleotide/3.85 parts lipomacrocycle (any one of lipoaimne listed in table 1 and 2 or known in arts)/0.42 parts DLinPE/0.21 parts DSG-PEG 2000/0.79 parts cholesterol (weight/weight). Another embodiment is the formulation consisting of 1 part polynucleotide/3.85 parts lipomacrocycle (any one of ipoazamacrocycle listed in table 1 and 2 or known in arts)/0.42 parts DLinPE/0.21 parts DPG-PEG 2000/0.79 parts cholesterol (weight/weight). Another embodiment is the formulation consisting of 1 part polynucleotide/2 parts DOTMA/6.6 parts lipomacrocycle (any one of lipomacrocycle listed in table 1 and 2 or known in arts)/2.2 parts DLinPE/14.4 parts DSPE-PEG 2000/0.6 parts cholesterol (weight/weight). Another embodiment is the formulation consisting of 1 part polynucleotide/5.5 parts lipomacrocycle (any one of lipomacrocycle s listed in table 1 and 2 or known in arts)/0.6 parts DLinPE/0.3 parts DSPE-PEG 2000/1.13 parts cholesterol (weight/weight).

This disclosure provides pharmaceutically acceptable nucleic acid compositions useful for therapeutic delivery of nucleic acids, plasmids, antisense nucleic acids, ribozymes, aptamers, antagomirs, siRNA, miRNA, gene-silencing iNAs and mixtures thereof. These compositions and methods may be used for prevention and/or treatment of diseases in a mammal.

The claimed lipid/nucleic acid formulations can be made by mixing lipids with nucleic acid, upon mixing with the lipids produce nucleic acid-lipid complexes that can be administered to animal for gene therapies using plasmid DNA as the nucleic acid, or for down-regulating a gene using antisense, ribozymes, antagomirs, siRNA, miRNA, iNA, or to inhibit other conditions using aptamers as the nucleic acid.

The present description provides another set of formulations and another method of formulation making. This disclosure also provides compositions and formulations for intracellular and in vivo delivery of drug agents for use, ultimately, as a therapeutic. The compounds and compositions of this disclosure are useful for delivery of drug agents to selected cells, tissues, organs or compartments in order to alter a disease state or a phenotype.

In some aspects, this disclosure provides compounds, compositions and methods to deliver polynucleotides such as DNA, RNA, antisense, aptamer, antagamer, plasmid, interfering nucleic acid (iNA), ribozyme, siRNA, microRNA (miRNA) to animal, tissues, organs, or/and cells to produce the response of down-regulation or up-regulation of gene expression.

One aspect of the description is a composition consisting of solid mixture of cationic lipids and a polynucleotide, wherein the cationic lipid molecules form a water-insoluble ionic complex with the polynucleotide, and wherein the number of cationic lipids is near the same as the number of nucleotide monomers of the polynucleotide. An embodiment of the description is the composition in which the cationic lipid is selected from the group consisting of N,N-dioleyl-N,N-dimethylammonium chloride (DODAC); N-(1-(2,3-dioleyloxy)propyl)-N,N,N-trimethylammonium chloride (DOTMA); N,N-dimethyl-(2,3-dioleyloxy)propylamine ("DODMA"); N,N-distearyl-N,N-dimethylammonium bromide ("DDAB"); N-(1-(2,3-dioleoyloxy)propyl)-N,N,N-trimethylammonium chloride ("DOTAP"); 3-(N—(N',N'-dimethylaminoethane)-carbamoyl)cholesterol (DC-Chol); N-(1,2-dimyristyloxyprop-3-yl)-N,N-dimethyl-N-hydroxyethyl ammonium bromide ("DMRIE"); 1,2-Dilinoleyloxy-N,N-dimethylaminopropane (DLinDMA); and 1,2-Dilinolenyloxy-N,N-dimethylaminopropane (DLenDMA), dioctadecyldimethylammonium (DODMA), distearyldimethylammonium (DSDMA), 1,2-dilinoleyloxy-N,N-dimethylaminopropane (DLinDMA), 1,2-dilinolenyloxy-N,N-dimethylaminopropane (DLenDMA), $N^4$-spermine cholesteryl carbamate (GL-67), $N^4$-spermidine cholstryl carbarnate (GL-53), 1-($N^4$-spermine)-2,3-dilaurylglycerol carbamate (GL-89) and mixtures thereof. Most preferably, the lipid is selected from the group consisting of DOTAP, DODAP, DLinDMA, DC-Chol, and DOTMA. Another aspect of the description is the composition in which the nucleic acid is selected from the group consisting of DNA, RNA, antisense, aptamer, antagamer, plasmid, iNA, ribozyme, siRNA, microRNA (miRNA), and mixtures thereof. Preferably, the composition is in the form of an anhydrous solid.

Another aspect of the description is the composition in which the mixture is made by a process of combining a cationic lipid with a polynucleotide in an aqueous solvent, producing a water-insoluble precipitate, isolating the precipitate, and drying the precipitate. One embodiment is the composition that is capable of being solubilized in an organic or polar aprotic solvent. Then, the dissolved polynucleotide/cationic lipid complex in an organic solvent can be further mixed with one or more lipids for making formulations. After removing the organic solvent, the dry formulation can be administrated to animals after hydration or dissolved in organic solvent which is not toxic to animal.

Another aspect of the description is a formulation comprising any of the above compositions and a phospholipid selected from the group consisting of phosphatidyl ethanolamine, phosphatidyl choline, sphinogomyelin and phosphatidyl inositol. The lipids can be uses in formulation include but not limited to phosphatidyl ethanolamine, phosphatidyl choline, phosphatidyl inositol and diphosphatidyl glycerol, such as 1,2-Dilauroyl-sn-glycerol (DLG); 1,2-Dimyristoyl-sn-glycerol (DMG); 1,2-Dipalmitoyl-sn-glycerol (DPG); 1,2-Distearoyl-sn-glycerol (DSG); 1,2-Dilauroyl-sn-glycero-3- phosphatidic acid (sodium salt; DLPA); 1,2-Dimyristoyl-sn-glycero-3-phosphatidic acid (sodium salt; DMPA); 1,2-Dipalmitoyl-sn-glycero-3-phosphatidic acid (sodium salt; DPPA); 1,2-Distearoyl-sn-glycero-3-phosphatidic acid (sodium salt; DSPA); 1,2-Diarachidoyl-sn-glycero-3-phosphocholine (DAPC); 1,2-Dilauroyl-sn-glycero-3-phosphocholine (DLPC); 1,2-Dimyristoyl-sn-glycero-3-phosphocholine (DMPC); 1,2-Dipalmitoyl-sn-glycero-O-ethyl-3-phosphocholine (chloride or triflate; DPePC); 1,2-Dipalmitoyl-sn-glycero-3-phosphocholine (DPPC); 1,2-Distearoyl-sn-glycero-3-phosphocholine (DSPC); 1,2-Dilauroyl-sn-glycero-3-phosphoethanolamine (DLPE); 1,2-Dimyristoyl-sn-glycero-3-phosphoethanolamine (DMPE); 1,2-Dipalmitoyl-sn-glycero-3-phosphoethanolamine (DPPE); 1,2-Distearoyl-sn-glycero-3-phosphoethanolamine (DSPE); 1,2-Dilauroyl-sn-glycero-3-phosphoglycerol (sodium salt; DLPG); 1,2-Dimyristoyl-sn-glycero-3-phosphoglycerol (sodium salt; DMPG); 1,2-Dimyristoyl-sn-glycero-3-phospho-sn-1-glycerol (ammonium salt; DMP-sn-1-G); 1,2-Dipalmitoyl-sn-glycero-3-phosphoglycerol (sodium salt; DPPG); 1,2-Distearoyl-sn-glycero-3-phosphoglycero (sodium salt; DSPG); 1,2-Distearoyl-sn-glycero-3-phospho-sn-1-glycerol (sodium salt; DSP-sn-1-G); 1,2-Dipalmitoyl-sn-glycero-3-phospho-L-serine (sodium salt; DPPS); 1-Palmitoyl-2-linoleoyl-sn-glycero-3-phosphocholine (PLinoPC); 1-Palmitoyl-2-oleoyl-sn-glycero-3-phosphocholine (POPC); 1-Palmitoyl-2-oleoyl-sn-glycero-3-phosphoglycerol (sodium salt; POPG); 1-Palmitoyl-2-oleoyl-sn-glycero-3-phosphoglycerol (sodium salt; POPG); 1-Palmitoyl-2-oleoyl-sn-glycero-3-phosphoglycerol (ammonium salt; POPG); 1-Palmitoyl-2-4-o-sn-glycero-3-phosphocholine (P-lyso-PC); 1-Stearoyl-2-lyso-sn-glycero-3-phosphocholine (S-lyso-PC); 1,2-didocosahexaenoyl-sn-glycero-3-phosphoethanolamine (22:6 PE); 1,2-diarachidonoyl-sn-glycero-3-phosphoethanolamine (20:4 PE); 1,2-dilinolenoyl-sn-glycero-3-phosphoethanolamine (18:3 PE); 1,2-dilinoleoyl-sn-glycero-3-phosphoethanolamine (DlinPE) 1,2-dipalmitoyl-sn-glycero-3-phosphoethanolamine (DPPE); 1,2-distearoyl-sn-glycero-3-phosphoethanolamine (DSPE); 1,2-dimyristoyl-sn-glycero-3-phosphoethanolamine (DMPE); and mixtures thereof.

Another aspect of the description is a formulation comprising any of the above compositions, and a PEG linked lipid, preferably a PEG-linked cholesterol, most preferably in which the PEG has a molecular weight between 200 and 5000 Da Another aspect of the description is a formulation comprising the any of the above compositions, and 1,2-dioleoyl-sn-glycero-3-phosphoethanolamine, cholesterol, and C16 PEG750 ceramide 1,2-dilinoleoyl-sn-glycero-3-phosphoethanolamine, cholesterol, and cholesterol-PEG; and 1,2-dilinoleoyl-sn-glycero-3-phosphoethanolamine, cholesterol, and DSPE-PEG 2000; 1,2-dilinoleoyl-sn-glycero-3-phosphoethanolamine, cholesterol, and DOPE-PEG 2000; or 1,2-dilinoleoyl-sn-glycero-3-phosphoethanolamine, cholesterol, cholesterol-PEG 660, and DSPE-PEG 2000

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin or other mucosal surfaces. In some aspects of this disclosure, the mucosal tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators.

Compositions of this disclosure may be administered in an aqueous solution as a nasal or pulmonary spray and may be dispensed in spray form by a variety of methods known to those skilled in the art. Pulmonary delivery of a composition of this disclosure is achieved by administering the composition in the form of drops, particles, or spray, which can be, for example, aerosolized, atomized, or nebulized. Particles of the composition, spray, or aerosol can be in a either liquid or solid form. Preferred systems for dispensing liquids as a nasal spray are disclosed in U.S. Pat. No. 4,511,069. Such formulations may be conveniently prepared by dissolving compositions according to the present disclosure in water to produce an aqueous solution, and rendering said solution sterile. The formulations may be presented in multi-dose containers. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or mixtures thereof.

Nasal and pulmonary spray solutions of the present disclosure typically comprise the drug or drug to be delivered, optionally formulated with a surface active agent, such as a nonionic surfactant (e.g., polysorbate-80), and one or more buffers. In some embodiments of the present disclosure, the nasal spray solution further comprises a propellant. The pH of the nasal spray solution may be from about pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this description is a pharmaceutical product which includes a solution containing a composition of this disclosure and an actuator for a pulmonary, mucosal, or intranasal spray or aerosol. The dosage form of the composition of this description can be liquid, in the form of droplets or an emulsion, or in the form of an aerosol. The dosage form of the composition of this description can be solid, which can be reconstituted in a liquid prior to administration. The solid can be administered as a powder. The solid can be in the form of a capsule, tablet or gel.

To formulate compositions for pulmonary delivery within the present description, the biologically active agent can be combined with various pharmaceutically acceptable additives, as well as a base or carrier for dispersion of the active agent(s). Examples of additives include pH control agents such as arginine, sodium hydroxide, glycine, hydrochloric acid, citric acid, and mixtures thereof. Other additives include local anesthetics (e.g., benzyl ethanol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g. maleic anhydride) with other monomers (e.g., methyl(meth)

acrylate, acrylic acid, etc.), hydrophilic vinyl polymers such as polyvinyl acetate, polyvinyl ethanol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters 4 such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, crosslinking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3000. Examples of hydrophilic low molecular weight compounds include polyol compounds, such as oligo-, di- and monosaccarides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, ethanols (e.g., oligovinyl ethanol, ethanol, ethylene glycol, propylene glycol, etc.), and mixtures thereof.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the biologically active agent may be administered in a time release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the disclosure can be brought about by including in the composition agents that delay absorption, for example, aluminum monosterate hydrogels and gelatin.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications and equivalents. In particular, this disclosure includes any combination of the features, terms, or elements of the various illustrative components and examples.

While this description has been described in relation to certain embodiments, and many details have been set forth for purposes of illustration, it will be apparent to those skilled in the art that this description includes additional embodiments, and that some of the details described herein may be varied considerably without departing from this description. This description includes such additional embodiments, modifications and equivalents. In particular, this description includes any combination of the features, terms, or elements of the various illustrative components and examples.

I. EXAMPLES

The following methods illustrate production of certain of the cationic lipids of the description. Those skilled in the art will recognize other methods to produce these compounds, and to produce also the other compounds of the description.

Example 1

Synthesis of Lipomacrocycle Compounds

Lipomacrocycle compounds were synthesized by combining cyclic amine compounds with epoxides in a glass vial equipped with a stirbar without solvents and heated to 90° C. The amines-sterol compounds chosen contain between two and ten amine functionalities, while the epoxides include varying chain lengths and feature unique functional groups and varying degrees of saturation of aliphatic chains and polyethylene glycol (PEG-2000). The reaction times varied from 24-72 hours at this temperature. The extent of the reaction could be controlled by the number of equivalents of epoxide added to the reaction mixture. For example, if the cyclic compound consists of six amines, then addition of six equivalents of epoxide would yield a cyclic compound core with six alkane chains linked. Addition of four equivalents of epoxide would yield only four chains linked by the same structure and other two points can be linked with one cholesterol and one PEG moiety separately or two cholesterol moieties. This was verified by thin layer chromatography (TLC), which showed primarily one product existing in the crude reaction mixtures set up as described.

Cholesterol carbamate formed by methods of ordinary skill was added to a cold stirring solution containing amine and triethylamine in chloroform. After stirring overnight at room temperature, the synthesized compound was extracted. The extracted compounds were further reacted with epoxides in a glass vial equipped with a stirbar without solvents and heated to 90° C. The amines chosen contain between two and eight amine functionalities, while the epoxides include varying chain lengths and feature unique functional groups and varying degrees of saturation of aliphatic chains and polyethylene glycol. The reaction times varied from 24-72 hours at this temperature. The extent of the reaction could be controlled by the number of equivalents of epoxide added to the reaction mixture. For example, one amine has a maximum of six points for substitution. Addition of six equivalents of epoxide would yield an amine core with six alkane chains linked. Addition of four equivalents of epoxide would yield only four chains linked by the same structure and other two points can be linked with one cholesterol and one PEG moiety or two cholesterol moieties. This was verified by thin layer chromatography (TLC), which showed primarily one product existing in the crude reaction mixtures set up as described.

Example 3

Preparation of Liposomes

Each liposome formulation was made by mixing lipids of each lipomacrocycle compound (Table 1) combined with DSPC, DMG-PEG 2K, and cholesterol at the weight ratio of 3.85:0.42:0.21:0.79 in ethanol and siRNA in water. Then 5% dextrose water was added in each formulation before dosing to mice.

Example 4

Preparation of Lipid Particles

Lipid Particle formulations were made by first mixed siRNA in an aqueous solution with DOTMA in organic solvent to produce a water-insoluble precipitate. After isolating and drying the precipitate, the precipitate was dissolved in chloroform and further mixed with other lipids as following: Each lipid particle formulation was consisting of 1 part DOTMA+siRNA complex/5 parts any lipomacrocycle compound (Table 1)/1.5 parts N 6-tetrakis (3-aminopropyl)-1,3-propanediamine cholesteryl carbamate/2.2 parts 1,2-dilinoleoyl-sn-glycero-3-phosphoethanolamine/10.08 parts cholesterol PEG-660/4.32 parts cholesterol PEG-660/0.6 parts cholesterol (weight/weight). All the components were dissolved in chloroform and mixed together. Then, the mixtures were dried overnight in Speedvac. The dried formulations were hydrated by adding in certain amount of 5% dextrose water before dosing to animals intravenously.

Example 5

In Vivo Gene Knockdown

All procedures used in animal studies conducted were approved by the Institutional Animal Care and Use Committee (IACUC) and were consistent with local, state and federal regulations as applicable. Mice, rats, and rabbits received siRNA formulations intravenously at dose volume of 0.2 ml, 1 ml, or 10 ml, respectively. Animals were sacrificed 2 to 7 days later. Tissues were harvested and mRNA was isolated with Turbocapture kit (Qiagen) for analyzing change of gene expression with real-time RT-PCR method (SensiMix SYBR One-Step Kit, Bioline). Serum was harvested for analyzing blood chemistry.

CD1 mice were dosed with lipid particle (Table 1) or liposome (Table 2) siRNA formulation intravenousely and the different tissues were harvested three days later. The gene expression was analyzed with real-time RT-PCR method (for liver, GAPDH as reference gene; for lung and bone marrow, GAPDG and β-actin as reference genes).

TABLE 1

Results of testing lipid particles prepared as in Example 4

| Compound | siRNA | dose (mg/kg) | Targeted mRNA remain in Liver |
|---|---|---|---|
| B1C1 | APOB | 0.8 | 0.82 |
| B1ch1 | APOB | 3 | 0.86 |
| B1Ch1C1 | SSB | 3.2 | 0.68 |
| B1ch1C3 | APOB | 3 | 0.12 |
| B1Ch1C3A | APOB | 3 | 0.65 |
| B1Ch2C1 | SSB | 3.2 | 0.59 |
| B1Ch2C2 | SSB | 3 | 0.66 |
| B1Ch2C3 | SSB | 3 | 0.43 |
| B1Ch2C3A | APOB | 3 | 0.48 |
| B2C1 | APOB | 0.8 | 0.52 |
| B2C3 | APOB | 0.8 | 1.01 |
| B2Ch2C1 | SSB | 3.2 | 0.49 |
| B2Ch2C3 | SSB | 3 | 0.42 |
| B2Ch2C3A | APOB | 3 | 0.95 |
| D1C1 | APOB | 1 | 0.14 |
| D1ch1 | APOB | 3 | 0.92 |
| D1ch1C3 | APOB | 3 | 0.19 |
| D1ch1C3A | APOB | 3 | 0.57 |
| M10C1 | SSB | 3.2 | 0.06 |
| M10C1 | APOB | 1 | 0.14 |
| M10C3 | SSB | 3 | 0.43 |
| M10C4 | SSB | 3 | 0.63 |
| M10C5 | APOB | 1 | 0.61 |
| M10C6 | APOB | 1 | 0.48 |
| M10C7 | APOB | 1 | 0.39 |
| M10C8 | APOB | 1 | 0.06 |
| M10ch1 | APOB | 3 | 0.39 |
| M10ch1C3 | APOB | 3 | 0.21 |
| M10ch1C3A | APOB | 3 | 0.30 |
| M11C1 | APOB | 1 | 0.24 |
| M11ch1 | APOB | 3 | 0.94 |
| M11ch1C3 | APOB | 3 | 0.18 |
| M11ch1C3A | APOB | 3 | 0.82 |
| M1C1 | SSB | 3.2 | 0.55 |
| M1C7 | SSB | 3.2 | 0.35 |
| M1ch1 | APOB | 3 | 0.80 |
| M1ch1C3 | APOB | 3 | 0.15 |
| M1ch1C3A | APOB | 3 | 0.70 |
| M2C1 | SSB | 3.2 | 0.43 |
| M2C7 | SSB | 3.2 | 0.91 |
| M2ch1 | APOB | 3 | 0.64 |
| M2ch1C3 | APOB | 3 | 0.17 |
| M2ch1C3A | APOB | 3 | 0.94 |
| M3C1 | SSB | 3.2 | 0.19 |
| M3C4 | SSB | 3.2 | 0.15 |
| M3C6 | SSB | 3.2 | 0.2 |
| M3C7 | SSB | 3.2 | 0.39 |
| M3ch1 | APOB | 3 | 1.13 |
| M3ch1C3 | APOB | 3 | 0.14 |
| M3ch1C3A | APOB | 3 | 0.72 |
| M4C1 | SSB | 3.2 | 0.3 |
| M4C7 | SSB | 3.2 | 0.75 |
| M4ch1 | APOB | 3 | 0.93 |
| M4ch1C3 | APOB | 3 | 0.22 |
| M4ch1C3A | APOB | 1 | 0.72 |
| M6C1 | SSB | 3.2 | 0.64 |
| M6ch1 | APOB | 3 | 0.86 |
| M6ch1C3 | APOB | 3 | 0.20 |
| M7C1 | SSB | 3.2 | 0.21 |
| M8C1 | SSB | 3.2 | 0.18 |
| M8ch1 | APOB | 3 | 0.92 |
| M8ch1C3 | APOB | 3 | 0.41 |
| M8ch1C3A | APOB | 3 | 0.93 |
| M9C1 | SSB | 3.2 | 0.2 |
| MdCh1C1 | SSB | 3.2 | 0.41 |
| MdCh1C2 | SSB | 3.2 | 0.49 |
| MdCh1C3 | APOB | 1 | 0.62 |
| MdCh1C3 | APOB | 1.5 | 0.38 |
| MdCh1C3 | SSB | 3.2 | 0.27 |
| MdCh1C4 | SSB | 3.2 | 0.54 |
| MdCh1C5 | SSB | 3.2 | 0.39 |
| MdCh1C6 | SSB | 3.2 | 0.31 |
| MdCh1C7 | SSB | 3.2 | 0.56 |
| MdCh2C1 | SSB | 3.2 | 0.69 |
| MdCh2C3A | APOB | 3 | 0.57 |

TABLE 1-continued

Results of testing lipid particles prepared as in Example 4

| Compound | siRNA | dose (mg/kg) | Targeted mRNA remain in Liver |
|---|---|---|---|
| NsC1 | APOB | 0.8 | 0.46 |
| Nsch1 | APOB | 3 | 0.84 |
| NsCh1C1 | APOB | 0.8 | 0.67 |
| NsCh1C2 | APOB | 0.8 | 0.73 |
| Nsch1C3 | APOB | 0.8 | 0.92 |
| Nsch1C3 | APOB | 3 | 0.12 |
| Nsch1C3A | APOB | 3 | 0.32 |
| NsCh1C4 | APOB | 0.8 | 0.88 |
| NsCh1C6 | APOB | 0.8 | 0.87 |
| S1Ch1C1 | SSB | 3.2 | 0.17 |
| S1Ch1C2 | APOB | 1.5 | 0.11 |
| S1Ch1C3 | SSB | 3 | 0.31 |
| S1Ch1C4 | SSB | 3 | 0.72 |
| SCh1C3A | APOB | 3 | 0.47 |
| T1C1 | APOB | 1 | 0.31 |
| T1C7 | SSB | 3.2 | 0.48 |
| T1C8 | APOB | 1 | 0.85 |
| T1ch1 | APOB | 3 | 1.13 |
| T1ch1C3 | APOB | 3 | 0.18 |
| T1ch1C3A | APOB | 3 | 0.81 |
| T2C1 | SSB | 3.2 | 0.21 |
| T2C4 | SSB | 3.2 | 1.22 |
| T2C6 | SSB | 3.2 | 0.86 |
| T2C7 | SSB | 3.2 | 0.59 |
| T2ch1 | APOB | 3 | 0.57 |
| T2ch1C3 | APOB | 3 | 0.35 |
| T2ch1C3A | APOB | 3 | 1.12 |
| T3C1 | SSB | 3.2 | 0.18 |
| T3C4 | SSB | 3.2 | 0.3 |
| T3C6 | SSB | 3.2 | 0.18 |
| T3C7 | SSB | 3.2 | 0.11 |
| T3Ch1C1 | SSB | 3.2 | 0.19 |
| T3Ch1C1A | APOB | 0.8 | 0.83 |
| T3Ch1C2 | SSB | 3 | 0.61 |
| T3Ch1C2A | APOB | 0.8 | 0.72 |
| T3Ch1C3 | SSB | 3 | 0.36 |
| T3Ch1C3A | APOB | 3 | 0.36 |
| T3Ch1C4A | APOB | 0.8 | 0.81 |
| T3Ch1C6A | APOB | 0.8 | 0.69 |
| T3Ch2C1 | SSB | 3.2 | 0.33 |
| T3Ch2C2 | SSB | 3.2 | 0.19 |
| T3Ch2C3 | APOB | 1 | 0.45 |
| T3Ch2C3 | SSB | 3.2 | 0.19 |
| T3Ch2C3A | APOB | 3 | 0.62 |
| T3Ch2C4 | SSB | 3.2 | 0.34 |
| T3Ch2C5 | SSB | 3.2 | 0.62 |
| T3Ch2C6 | SSB | 3.2 | 0.6 |
| T3Ch2C7 | SSB | 3.2 | 0.58 |
| T4C1 | SSB | 3.2 | 0.1 |
| T4C2 | SSB | 3.2 | 0.29 |
| T4C4 | SSB | 3.2 | 0.19 |
| T4C5 | SSB | 3.2 | 0.35 |
| T4C6 | SSB | 3.2 | 0.19 |
| T4C7 | SSB | 3.2 | 0.2 |
| T4Ch1C1 | APOB | 1 | 0.32 |
| T4Ch1C1 | SSB | 3.2 | 0.24 |
| T4Ch1C2 | SSB | 3 | 0.30 |
| T4Ch1C3 | SSB | 3 | 0.32 |
| T4Ch1C3A | APOB | 3 | 0.37 |
| T4Ch1C4 | SSB | 3 | 0.54 |
| T4Ch2C1 | SSB | 3.2 | 0.2 |
| T4Ch2C1A | APOB | 0.8 | 0.71 |
| T4Ch2C2 | SSB | 3 | 0.44 |
| T4Ch2C2A | APOB | 0.8 | 0.71 |
| T4Ch2C3 | SSB | 3 | 0.32 |
| T4Ch2C3A | APOB | 3 | 0.35 |
| T4Ch2C4A | APOB | 0.8 | 0.71 |
| T4Ch2C6A | APOB | 0.8 | 0.71 |
| T5ch1 | APOB | 3 | 0.39 |
| T5Ch1C1A | APOB | 0.8 | 0.59 |
| T5Ch1C2A | APOB | 0.8 | 0.93 |
| T5ch1C3 | APOB | 3 | 0.26 |
| T5ch1C3A | APOB | 3 | 0.59 |
| T5Ch1C4A | APOB | 0.8 | 1.02 |
| T5Ch1C6A | APOB | 0.8 | 0.92 |
| T5ch2 | APOB | 2.5 | 0.52 |
| TaC1 | APOB | 0.8 | 0.81 |

The 1st letter such as B1, B2 designate the head group. The last letter such as C1, C2 designate the tail group. The letter ch1 or ch2 indicates the compound has one or two cholesterol. The compound such as B1Ch1C1 and B2ch2C1 designates that the head B1 or B2 is linked with one or two cholesterol and all the remain reaction sites filled with tail C1. The compound such as B1Ch1C1A and B2ch2C1A designates that the head B1 or B2 is linked with one or two cholesterol and one C1 tail.

Based on the results of Table 1, the performance of the lipid molecules are ranked as follows:

Head group selection from 1 (best) to 4 (fair):
1. D1, T1, M10,
2. B1, S1, T3, T4, M1, M3, M11
3. B1, Ns, Md, T2, T5, M2, M4, M6, M7, M8, M9,
4. B2

Tail group selection:
Best: C1, C2, C3, C4, C6, C7, C8, Cholesterol.
Fair: C5

The best compounds are M10C1, M10C8, T1C1, and D1C1.

TABLE 2

Results of testing liposomal formulation prepared as in Example 3

| Compound | siRNA | dose (mg/kg) | Targeted mRNA remain in liver |
|---|---|---|---|
| B1C1 | SSB | 3.2 | 0.13 |
| B1C2 | SSB | 3.2 | 0.68 |
| B1C3 | SSB | 3.2 | 0.12 |
| B1C4 | SSB | 3.2 | 0.11 |
| B1C5 | SSB | 3.2 | 0.36 |
| B1C6 | SSB | 3.2 | 0.13 |
| B1C7 | SSB | 3.2 | 0.14 |
| B2C1 | SSB | 3.2 | 0.06 |
| B2C2 | SSB | 3.2 | 0.36 |
| B2C3 | SSB | 3.2 | 0.11 |
| B2C4 | SSB | 3.2 | 0.11 |
| B2C5 | SSB | 3.2 | 0.14 |
| B2C6 | SSB | 3.2 | 0.08 |
| B2C7 | SSB | 3.2 | 0.06 |
| D1C1 | SSB | 3.2 | 0.08 |
| D1C2 | SSB | 3.2 | 0.11 |
| D1C3 | SSB | 3.2 | 0.18 |
| D1C4 | SSB | 3.2 | 0.14 |
| D1C5 | SSB | 3.2 | 0.28 |
| D1C6 | SSB | 3.2 | 0.27 |
| D1C7 | SSB | 3.2 | 0.52 |
| M10C1 | SSB | 3.2 | 0.07 |
| M11C1 | SSB | 3.2 | 0.19 |
| M1C1 | SSB | 3.2 | 0.89 |
| M1C2 | SSB | 3.2 | 0.67 |
| M1C3 | SSB | 3.2 | 0.64 |
| M1C4 | SSB | 3.2 | 0.54 |
| M1C5 | SSB | 3.2 | 0.6 |
| M1C6 | SSB | 3.2 | 0.57 |
| M1C7 | SSB | 3.2 | 0.47 |
| M2C1 | SSB | 3.2 | 0.31 |
| M2C2 | SSB | 3.2 | 0.2 |
| M2C3 | SSB | 3.2 | 0.18 |
| M2C4 | SSB | 3.2 | 0.33 |
| M2C5 | SSB | 3.2 | 0.87 |
| M2C6 | SSB | 3.2 | 0.92 |

TABLE 2-continued

Results of testing liposomal formulation prepared as in Example 3

| Compound | siRNA | dose (mg/kg) | Targeted mRNA remain in liver |
|---|---|---|---|
| M2C7 | SSB | 3.2 | 0.63 |
| M3C1 | SSB | 3.2 | 0.81 |
| M3C2 | SSB | 3.2 | 0.62 |
| M3C3 | SSB | 3.2 | 0.28 |
| M3C4 | SSB | 3.2 | 0.67 |
| M3C5 | SSB | 3.2 | 0.58 |
| M3C6 | SSB | 3.2 | 0.45 |
| M3C7 | SSB | 3.2 | 1.13 |
| M4C1 | SSB | 3.2 | 0.96 |
| M4C2 | SSB | 3.2 | 0.95 |
| M4C3 | SSB | 3.2 | 0.9 |
| M4C4 | SSB | 3.2 | 0.88 |
| M4C5 | SSB | 3.2 | 0.94 |
| M4C6 | SSB | 3.2 | 0.79 |
| M4C7 | SSB | 3.2 | 0.86 |
| M6C1 | SSB | 3.2 | 0.98 |
| M6C2 | SSB | 3.2 | 0.8 |
| M6C3 | SSB | 3.2 | 0.49 |
| M6C4 | SSB | 3.2 | 0.75 |
| M6C5 | SSB | 3.2 | 0.63 |
| M6C6 | SSB | 3.2 | 0.8 |
| M7C1 | SSB | 3.2 | 0.27 |
| M8C1 | SSB | 3.2 | 0.69 |
| M9C1 | SSB | 3.2 | 0.3 |
| MdC1 | SSB | 3.2 | 0.15 |
| MdC2 | SSB | 3.2 | 0.25 |
| MdC3 | SSB | 3.2 | 0.24 |
| MdC4 | SSB | 3.2 | 0.16 |
| MdC5 | SSB | 3.2 | 0.45 |
| MdC6 | SSB | 3.2 | 1.1 |
| MdC7 | SSB | 3.2 | 0.25 |
| NsC1 | SSB | 3.2 | 0.13 |
| NsC2 | SSB | 3.2 | 0.1 |
| NsC3 | SSB | 3.2 | 0.23 |
| NsC4 | SSB | 3.2 | 0.13 |
| NsC5 | SSB | 3.2 | 0.37 |
| NsC6 | SSB | 3.2 | 0.69 |
| NsC7 | SSB | 3.2 | 0.1 |
| S1C1 | SSB | 3.2 | 0.07 |
| S1C2 | SSB | 3.2 | 0.1 |
| S1C3 | SSB | 3.2 | 0.1 |
| S1C4 | SSB | 3.2 | 0.14 |
| S1C5 | SSB | 3.2 | 0.59 |
| S1C6 | SSB | 3.2 | 0.1 |
| S1C7 | SSB | 3.2 | 0.58 |
| T1C1 | SSB | 3.2 | 0.09 |
| T1C2 | SSB | 3.2 | 0.75 |
| T1C3 | SSB | 3.2 | 0.1 |
| T1C4 | SSB | 3.2 | 0.28 |
| TIC5 | SSB | 3.2 | 0.6 |
| T1C6 | SSB | 3.2 | 0.14 |
| T1C7 | SSB | 3.2 | 0.46 |
| T1C8 | SSB | 3.2 | 0.13 |
| T2C1 | SSB | 3.2 | 0.44 |
| T2C2 | SSB | 3.2 | 0.74 |
| T2C3 | SSB | 3.2 | 0.29 |
| T2C4 | SSB | 3.2 | 0.58 |
| T2C5 | SSB | 3.2 | 0.71 |
| T2C6 | SSB | 3.2 | 0.66 |
| T2C7 | SSB | 3.2 | 0.81 |
| T3C1 | SSB | 3.2 | 0.13 |
| T3C2 | SSB | 3.2 | 0.48 |
| T3C3 | SSB | 3.2 | 0.3 |
| T3C4 | SSB | 3.2 | 0.1 |
| T3C5 | SSB | 3.2 | 0.46 |
| T3C6 | SSB | 3.2 | 0.08 |
| T3C7 | SSB | 3.2 | 0.31 |
| T4C1 | SSB | 3.2 | 0.12 |
| T4C10 | APOB | 3 | 0.82 |
| T4C11 | APOB | 3 | 1.07 |
| T4C13 | APOB | 3 | 1.12 |
| T4C14 | APOB | 3 | 0.92 |
| T4C15 | APOB | 3 | 0.94 |
| T4C16 | APOB | 3 | 0.79 |
| T4C18 | APOB | 3 | 1.56 |
| T4C19 | APOB | 3 | 1.12 |
| T4C2 | SSB | 3.2 | 0.17 |
| T4C3 | SSB | 3.2 | 0.12 |
| T4C4 | APOB | 1 | 0.12 |
| T4C5 | SSB | 3.2 | 0.35 |
| T4C6 | SSB | 3.2 | 0.1 |
| T4C7 | SSB | 3.2 | 0.14 |
| T4C8 | APOB | 1 | 0.77 |
| T4Ch1C1 | SSB | 3.2 | 0.55 |
| T5C1 | SSB | 3.2 | 0.13 |
| T5C2 | SSB | 3.2 | 0.1 |
| T5C3 | SSB | 3.2 | 0.43 |
| T5C4 | SSB | 3.2 | 0.41 |
| T5C5 | SSB | 3.2 | 0.71 |
| T5C6 | SSB | 3.2 | 0.33 |
| T5C7 | SSB | 3.2 | 0.56 |
| TaC1 | SSB | 3.2 | 0.1 |
| TaC2 | SSB | 3.2 | 0.13 |
| TaC3 | SSB | 3.2 | 0.19 |
| TaC4 | SSB | 3.2 | 0.12 |
| TaC5 | SSB | 3.2 | 0.46 |
| TaC6 | SSB | 3.2 | 0.17 |
| TaC7 | SSB | 3.2 | 0.33 |

Based on the results of Table 2, the performance of the lipid molecules are ranked as follows:

Head group selection from 1 (best) to 3 (fair):
1. D1, T3, T4, T1, B2, M10,
2. B1, Md, Ns, S1, T5, Ta, M2, M11,
3. T2, M3, M7, M9

Tail group selection:
Best: C1, C2, C3, C4, C6, C7, C8
Fair: C5

The best performing compounds are D1C1, T1C1, T1C6, T4C4, B2C1, B2C6, B2C7, and M10C1.

What is claimed:

1. An aqueous liquid composition, comprising i) a therapeutic compound comprising a nucleic acid and ii) a macrocyclic lipid, which macrocyclic lipid is formed by reacting a cyclic compound of formula I

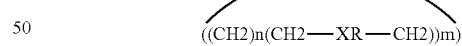

((CH2)n(CH2—XR—CH2))m)    I with an epoxide of formula II or III

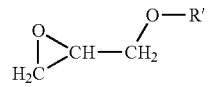

II

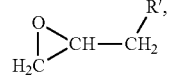

III wherein X is N, R is selected from the group consisting of H, a linear or branched alkyl, an aryl, a cholesterol, $CH_2CONH_2$, $CH_2CONHCH_3$, $CH_2CON(CH_3)_2$, a methylene bridge between a pair of the amino groups of the cyclic compound, or an ethylene bridge between pairs of amino groups of the cyclic compound;

wherein more than one R group may occur in the macrocyclic lipid;

wherein m=4 to 6, wherein for every repeat of the CH$_2$—XR—CH$_2$ group, n is 0 or 1; and wherein R' is C$_7$ to C$_{14}$.

2. The aqueous liquid composition of claim 1, wherein the nucleic acid is an RNA molecule.

3. The aqueous liquid composition of claim 2, wherein the nucleic acid is a siRNA molecule.

4. The aqueous liquid composition of claim 1, wherein the cyclic compound is selected from the group consisting of:

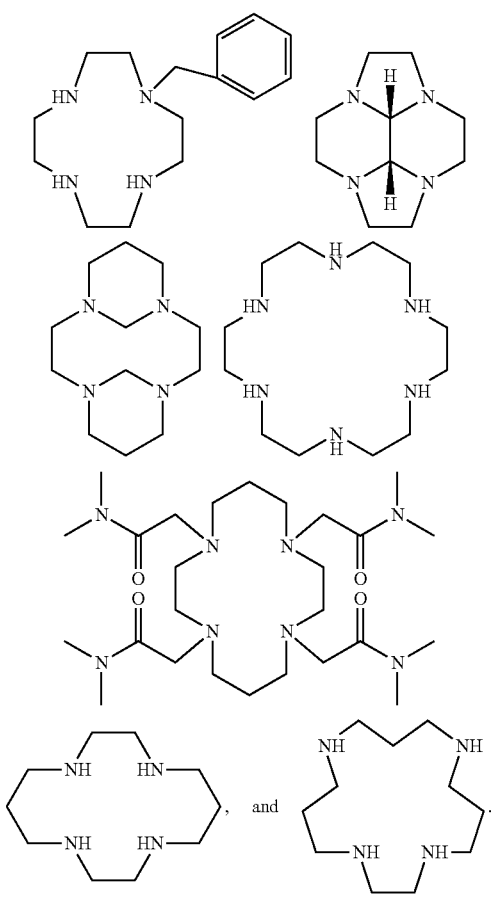

5. The aqueous liquid composition of claim 1, wherein the epoxide compound is selected from the group consisting of:

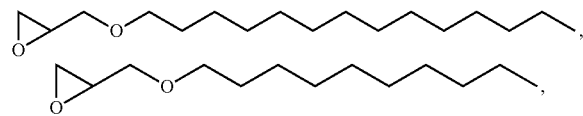

-continued

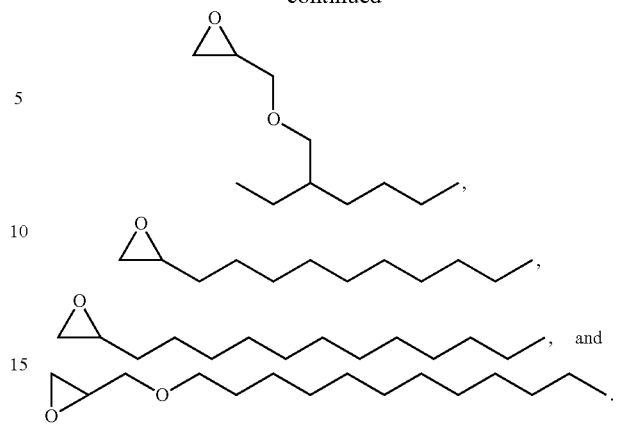

6. An aqueous liquid composition, comprising a liposome or a lipid particle, a nucleic acid, and a macrocyclic lipid, which macrocyclic lipid is formed by reacting a cyclic compound of formula I

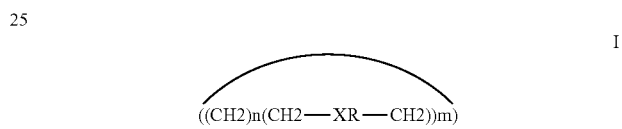

with an epoxide of formula II or III

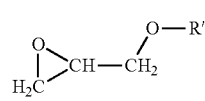

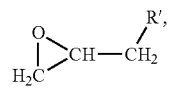

wherein X is N, R is selected from a group consisting of H, a linear or branched alkyl, an aryl, a cholesterol, CH$_2$CONH$_2$, CH$_2$CONHCH$_3$, CH$_2$CON(CH$_3$)$_2$, a methylene bridge between a pair of the amino groups of the cyclic compound, or an ethylene bridge between pairs of amino groups of the cyclic compound;

wherein more than one R group may occur in the macrocyclic lipid;

wherein m=4 to 6, wherein for every repeat of the CH$_2$—XR—CH$_2$ group, n is 0 or 1; and wherein R' is C$_7$ to C$_{14}$.

7. The aqueous liquid composition of claim 6, wherein the nucleic acid is an RNA molecule.

8. The aqueous liquid composition of claim 7, wherein the nucleic acid is a siRNA molecule.

9. The aqueous liquid composition of claim 6, wherein the cyclic compound is selected from the group consisting of:

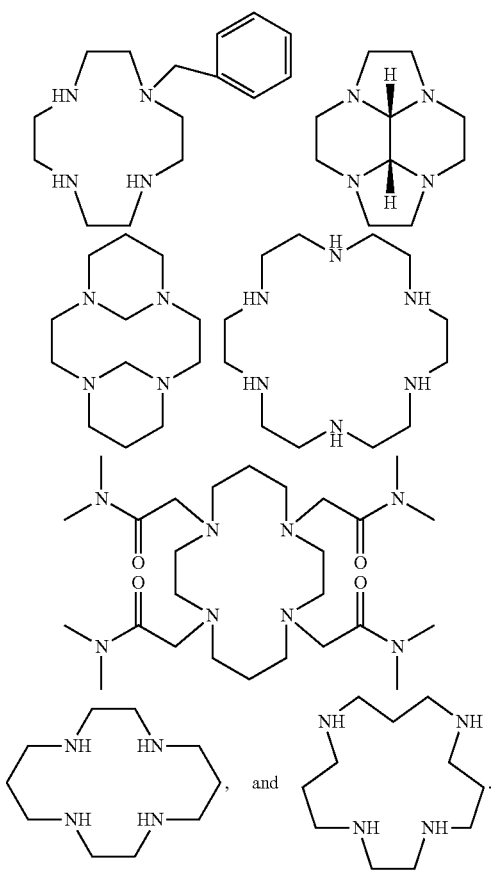

10. The aqueous liquid composition according to claim 1, wherein the macrocyclic lipid is in a lipid-polynucleotide particle comprising a lipid and a polynucleotide.

11. The aqueous liquid composition according to claim 1, wherein the macrocyclic lipid is a component of a liposome or a lipid particle.

12. The aqueous liquid composition according to claim 2, wherein the macrocyclic lipid is in a lipid-polynucleotide particle comprising a lipid and a polynucleotide.

13. The aqueous liquid composition according to claim 3, wherein the macrocyclic lipid is in a lipid-polynucleotide particle comprising a lipid and a polynucleotide.

14. The aqueous liquid composition according to claim 4, wherein the macrocyclic lipid is in a lipid-polynucleotide particle comprising a lipid and a polynucleotide.

15. The aqueous liquid composition according to claim 5, wherein the macrocyclic lipid in a lipid-polynucleotide particle comprising a lipid and a polynucleotide.

16. The aqueous liquid composition according to claim 6, wherein the macrocyclic lipid is in a lipid-polynucleotide particle comprising a lipid and a polynucleotide.

17. The aqueous liquid composition according to claim 7, wherein the macrocyclic lipid is in a lipid-polynucleotide particle comprising a lipid and a polynucleotide.

18. The aqueous liquid composition according to claim 8, wherein the macrocyclic lipid is in a lipid-polynucleotide particle comprising a lipid and a polynucleotide.

19. The aqueous liquid composition according to claim 9, wherein the macrocyclic lipid is in a lipid-polynucleotide particle comprising a lipid and a polynucleotide.

20. The aqueous liquid composition according to claim 12, wherein the polynucleotide is an RNA molecule.

21. The aqueous liquid composition according to claim 13, wherein the polynucleotide is an RNA molecule.

22. The aqueous liquid composition according to claim 14, wherein the polynucleotide is an RNA molecule.

23. The aqueous liquid composition according to claim 15, wherein the polynucleotide is an RNA molecule.

24. The aqueous liquid composition according to claim 16, wherein the polynucleotide is an RNA molecule.

25. The aqueous liquid composition according to claim 17, wherein the polynucleotide is an RNA molecule.

26. The aqueous liquid composition according to claim 18, wherein the polynucleotide is an RNA molecule.

27. The aqueous liquid composition according to claim 19, wherein the polynucleotide is an RNA molecule.

28. The aqueous liquid composition of claim 20, wherein the RNA molecule is an siRNA molecule.

29. The aqueous liquid composition of claim 21, wherein the RNA molecule is an siRNA molecule.

30. The aqueous liquid composition of claim 22, wherein the RNA molecule is an siRNA molecule.

31. The aqueous liquid composition of claim 23, wherein the RNA molecule is an siRNA molecule.

32. The aqueous liquid composition of claim 24, wherein the RNA molecule is an siRNA molecule.

33. The aqueous liquid composition of claim 25, wherein the RNA molecule is an siRNA molecule.

34. The aqueous liquid composition of claim 26, wherein the RNA molecule is an siRNA molecule.

35. The aqueous liquid composition of claim 27, wherein the RNA molecule is an siRNA molecule.

36. The aqueous liquid composition according to claim 2, wherein the macrocyclic lipid is a component of a liposome or a lipid particle.

37. The aqueous liquid composition according to claim 3, wherein the macrocyclic lipid is a component of a liposome or a lipid particle.

38. The aqueous liquid composition according to claim 4, wherein the macrocyclic lipid is a component of a liposome or a lipid particle.

39. The aqueous liquid composition according to claim 5, wherein the macrocyclic lipid is a component of a liposome or a lipid particle.

40. The aqueous liquid composition according to claim 6, wherein the macrocyclic lipid is a component of a liposome or a lipid particle.

41. The aqueous liquid composition according to claim 7, wherein the macrocyclic lipid is a component of a liposome or a lipid particle.

42. The aqueous liquid composition according to claim 8, wherein the macrocyclic lipid is a component of a liposome or a lipid particle.

43. The aqueous liquid composition according to claim 9, wherein the macrocyclic lipid is a component of a liposome or a lipid particle.

44. The aqueous liquid composition of claim 6, wherein the epoxide compound is selected from the group consisting of:

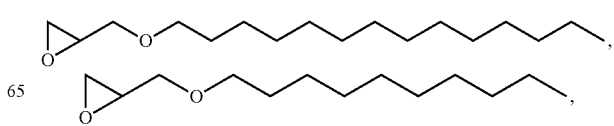

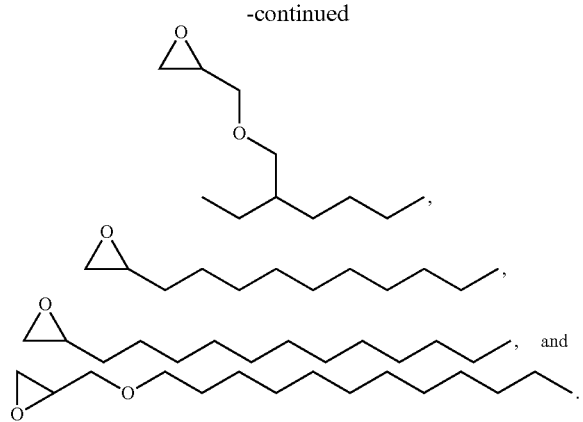

45. An aqueous liquid composition, comprising a liposome or lipid particle, a polynucleotide comprising DNA, and a macrocyclic lipid, which macrocyclic lipid is formed by reacting a cyclic compound of formula I

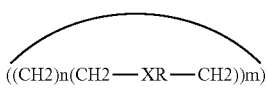
I with an epoxide of formula II or III

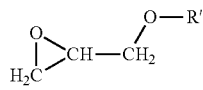
II

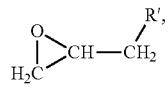
III wherein X is N, R is selected from a group consisting of H, a linear or branched alkyl, an aryl, a cholesterol, CH2CONH2, CH2CONHCH3, $CH_2CON(CH_3)_2$, a methylene bridge between a pair of the amino groups of the cyclic compound, or an ethylene bridge between pairs of amino groups of the cyclic compound;
wherein more than one R group may occur in the macrocyclic lipid;
wherein m=4 to 6,
wherein for every repeat of the CH2-XR—CH2 group, n is 0 or 1; and
wherein R' is $C_7$ to $C_{14}$.

46. The aqueous liquid composition of claim 45, wherein the liposome or lipid particle comprises a polynucleotide not comprising DNA.

47. The aqueous liquid composition of claim 46, wherein the polynucleotide is a siRNA molecule.

48. The aqueous liquid composition of claim 45, wherein the aqueous liquid composition is a pharmaceutical composition.

49. The aqueous liquid composition of claim 45, wherein the macrocyclic lipid is selected from the group consisting of:

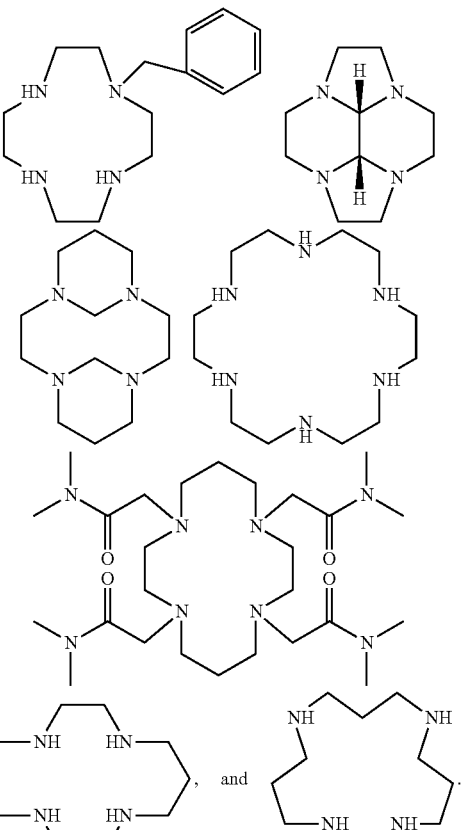

50. The aqueous liquid composition of claim 45, wherein the epoxide compound is selected from the group consisting of:

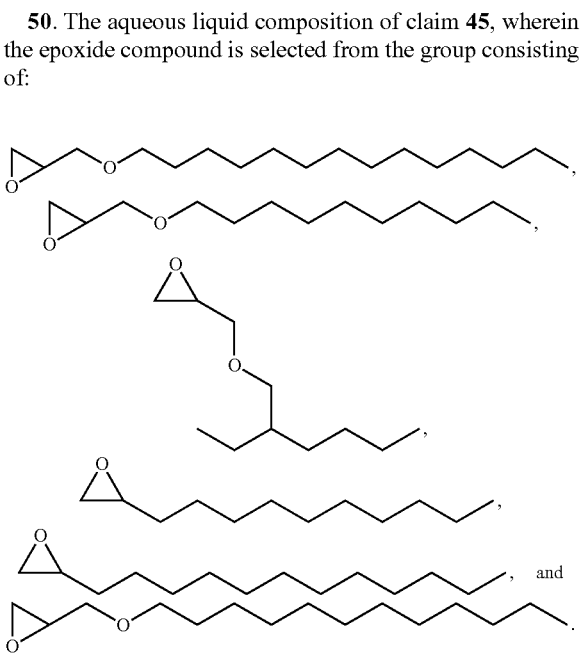

* * * * *